(12) United States Patent
Oomori et al.

(10) Patent No.: US 7,307,725 B2
(45) Date of Patent: Dec. 11, 2007

(54) SURFACE INSPECTION APPARATUS, POLARIZATION ILLUMINATING DEVICE AND LIGHT-RECEIVING DEVICE

(75) Inventors: Takeo Oomori, Sagamihara (JP); Hideo Hirose, Shiraoka-machi (JP); Yasuharu Nakajima, Yokohama (JP); Kenzo Chiaki, Kawasaki (JP); Tatsumi Satou, Kawasaki (JP)

(73) Assignee: Nikon Corporation, Tokyo (JP)

( * ) Notice: Subject to any disclaimer, the term of this patent is extended or adjusted under 35 U.S.C. 154(b) by 388 days.

(21) Appl. No.: 11/150,385

(22) Filed: Jun. 13, 2005

(65) Prior Publication Data
US 2005/0280806 A1    Dec. 22, 2005

(30) Foreign Application Priority Data

| Jun. 16, 2004 | (JP) | ............................. 2004-178880 |
| Nov. 9, 2004 | (JP) | ............................. 2004-324688 |
| Mar. 23, 2005 | (JP) | ............................. 2005-084290 |
| May 11, 2005 | (JP) | ............................. 2005-139068 |

(51) Int. Cl.
*G01J 4/00* (2006.01)
*G02B 5/30* (2006.01)

(52) U.S. Cl. ..................... 356/369; 356/364; 359/437

(58) Field of Classification Search ........ 356/364–370; 359/437; 362/19
See application file for complete search history.

(56) References Cited

U.S. PATENT DOCUMENTS 4,864,123 A * 9/1989 Mizutani et al. ............ 250/225
6,512,579 B2 * 1/2003 Oomori et al. ............ 356/237.5
6,646,735 B2 * 11/2003 Fukazawa et al. ........ 356/237.4
6,784,991 B2 * 8/2004 Rotter et al. ................. 356/369
6,831,743 B2 * 12/2004 Aspnes et al. ............... 356/369
2003/0035350 A1 * 2/2003 Ogasawara et al. ....... 369/44.23

FOREIGN PATENT DOCUMENTS

JP        10-232122         9/1998

* cited by examiner

*Primary Examiner*—Gregory J. Toatley, Jr.
*Assistant Examiner*—Jarreas Underwood
(74) *Attorney, Agent, or Firm*—Oliff & Beridge, PLC

(57) ABSTRACT

A surface inspection apparatus includes: a light source unit that emits a divergent light flux of predetermined linearly polarized light to be used to illuminate a test substrate; a first optical member that allows the divergent light flux of the predetermined linearly polarized light to enter therein with a predetermined angle of incidence and then guides a light flux to the test substrate; a second optical member that allows a light flux from the test substrate to enter therein, emits a convergent light flux thereof with a predetermined angle of emergence and forms an image at a specific surface; an extraction unit that extracts linearly polarized light in the convergent light flux from the second optical member, which is perpendicular to the predetermined linearly polarized light; a light-receiving unit that receives an image of the test substrate formed via the second optical member and the extraction unit; and at least one polarization correcting member disposed within a light path extending between the light source unit and the light-receiving unit, which corrects a disruption of a polarization plane attributable to the first optical member and the second optical member.

20 Claims, 14 Drawing Sheets

↔ : VIBRATION PLANE

↔ : VIBRATION PLANE

PHASE DIFFERENCE $\phi = 2\pi/\lambda \, (t1-t2) \, \Delta n$ $\Delta n$: DIFFERENCE BETWEEN REFRACTIVE INDICES OF ORDINARY RAYS AND EXTRAORDINARY RAYS

CRYSTAL AXES

SURFACE INSPECTION APPARATUS, POLARIZATION ILLUMINATING DEVICE AND LIGHT-RECEIVING DEVICE

INCORPORATION BY REFERENCE

The disclosures of the following priority applications are herein incorporated by reference:
Japanese Patent Application No. 2004-178880 filed Jun. 16, 2004
Japanese Patent Application No. 2004-324688 filed Nov. 9, 2004
Japanese Patent Application No. 2005-084290 filed Mar. 23, 2005
Japanese Patent Application No. 2005-139068 filed May 11, 2005

BACKGROUND OF THE INVENTION

1. Field of the Invention

The present invention relates to a surface inspection apparatus, a polarization illuminating device and a light-receiving device used to detect defects such as irregularities and scars at a substrate surface during a process of manufacturing semiconductor elements or the like.

2. Description of Related Art

Inspection apparatuses used to inspect wafer surfaces during a process of manufacturing semiconductor circuit elements and the like to detect any defects in repetitive patterns formed at the surfaces known in the related art include those that use diffraction. In an apparatus in which diffraction light is used, the tilt angle of the stage must be adjusted in correspondence to the pattern pitch. In addition, in order to inspect an extremely minute pattern, the wavelength of the illuminating light must be reduced.

SUMMARY OF THE INVENTION

However, if the inspection of patterns with an extremely small pitch of repetition (i.e., extremely small line-and-space dimensions in wiring patterns and the like) is to be enabled by reducing the wavelength of the illuminating light, the types of light sources that can be used become limited to expensive and large-scale light sources. There is an additional problem in that it also limits the materials that can be used to form optical elements to constitute the illuminating system and the light-receiving system to costly materials.

The present invention provides a surface inspection apparatus, a polarization illuminating device and a light-receiving device which can be used to inspect a pattern with an extremely small repetition pitch with a high level of reliability without reducing the wavelength of the illuminating light.

According to the 1st aspect of the invention, a surface inspection apparatus comprises: a light source unit that emits a divergent light flux of predetermined linearly polarized light to be used to illuminate a test substrate; an optical member that allows the divergent light flux of the predetermined linearly polarized light to enter therein with a principle ray of the divergent light flux achieving a predetermined angle of incidence and then guides a light flux to the test substrate; a light-receiving unit that receives linearly polarized light in a light flux from the test substrate, which is polarized along a direction perpendicular to a polarization direction of the predetermined linearly polarized light; at least one polarization correcting member disposed within a light path extending between the light source unit and the light-receiving unit, which corrects a disruption of a polarization plane attributable to the optical member; and an inspection unit that inspects a surface of the test substrate based upon the light received at the light-receiving unit.

According to the 2nd aspect of the invention, a surface inspection apparatus comprises: a light source unit that emits a light flux of predetermined linearly polarized light to be used to illuminate a test substrate; an optical member disposed at a position that allows a light flux from the test substrate to enter the optical member, through which the light flux from the test substrate is emitted as a convergent light flux with a principle ray of the convergent light flux achieving a predetermined angle of emergence; a light-receiving unit that receives linearly polarized light in the convergent light flux from the optical member, which is polarized along a direction perpendicular to a polarization direction of the predetermined linearly polarized light; at least one polarization correcting member disposed within a light path extending between the light source unit and the light-receiving unit, which corrects a disruption of a polarization plane attributable to the optical member; and an inspection unit that inspects a surface of the test substrate based upon the light received at the light-receiving unit.

According to the 3rd aspect of the invention, a surface inspection apparatus comprises: a light source unit that emits a divergent light flux of predetermined linearly polarized light to be used to illuminate a test substrate; a first optical member that allows the divergent light flux of the predetermined linearly polarized light to enter therein with a predetermined angle of incidence and then guides a light flux to the test substrate; a second optical member that allows a light flux from the test substrate to enter therein, emits a convergent light flux thereof with a predetermined angle of emergence and forms an image at a specific surface; an extraction unit that extracts linearly polarized light in the convergent light flux from the second optical member, which is perpendicular to the predetermined linearly polarized light; a light-receiving unit that receives an image of the test substrate formed via the second optical member and the extraction unit; and at least one polarization correcting member disposed within a light path extending between the light source unit and the light-receiving unit, which corrects a disruption of a polarization plane attributable to the first optical member and the second optical member.

According to the 4th aspect of the invention, in the surface inspection apparatus according to the 1st aspect, it is preferred that the polarization correcting member is disposed within the divergent light flux with a tilt toward a side opposite from a direction along which the optical member is tilted relative to the principle ray of the divergent light flux.

According to the 5th aspect of the invention, in the surface inspection apparatus according to the 2nd aspect, it is preferred that the polarization correcting member is disposed within the convergent light flux with a tilt toward a side opposite from a direction along which the optical member is tilted relative to the principle ray of the convergent light flux.

According to the 6th aspect of the invention, in the surface inspection apparatus according to any one of the above aspects, it is preferred that there is further provided a holding member that holds the polarization correcting member so as to allow at least either a direction or an angle of tilt with which the polarization correcting member is set to be adjustable.

According to the 7th aspect of the invention, in the surface inspection apparatus according to any one of the above aspects, it is preferred that the polarization correcting member is a plane parallel glass plate disposed at an inclination relative to a surface of the optical member.

According to the 8th aspect of the invention, in the surface inspection apparatus according to any one of the above aspects, it is preferred that the polarization correcting member is disposed at an inclination relative to a plane perpendicular to an optical axis of the optical member and is constituted with two birefringent plane parallel crystal plates pasted together so as to set crystal axes thereof perpendicular to each other.

According to the 9th aspect of the invention, in the surface inspection apparatus according to any one of the above aspects, it is preferred that the polarization correcting member is disposed at an inclination relative to a plane perpendicular to an optical axis of the optical member and is constituted with two wedge-shaped birefringent crystals pasted together so as to set crystal axes thereof perpendicular to each other and also to form a plane parallel plate.

According to the 10th aspect of the invention, in the surface inspection apparatus according to any one of the above aspects, it is preferred that stress-strain is set at the polarization correcting member disposed between the light source unit and the light-receiving unit.

According to the 11th aspect of the invention, in the surface inspection apparatus according to the 10th aspect, it is preferred that the stress-strain set at the polarization correcting member can be fixed to an arbitrary value.

According to the 12th aspect of the invention, in the surface inspection apparatus according to any one of the above aspects, it is preferred that a parallel light flux entering the optical member becomes convergent by the optical member.

According to the 13th aspect of the invention, a polarization illuminating device comprises: a light source unit that emits a divergent light flux of linearly polarized light; an optical member that allows the divergent light flux of the linearly polarized light generated at the light source unit to enter therein with a predetermined angle of incidence and then guides a light flux to a test substrate; and a polarization correcting member disposed within a light path extending between the light source unit and the test substrate, which corrects a disruption of a polarization plane attributable to the optical member.

According to the 14th aspect of the invention, a light-receiving device comprises: an optical member that allows a light flux originating from a test substrate and containing a specific polarization component to enter therein and emits a convergent light flux thereof with a predetermined angle of emergence; a light-receiving unit that receives linearly polarized light in the light flux from the optical member; and a polarization correcting member disposed within a light path extending between the test substrate and the light-receiving unit, which corrects a disruption of a polarization plane attributable to the optical member.

DESCRIPTION OF PREFERRED EMBODIMENTS

First Embodiment

The following is a detailed explanation of the principle of a surface inspection apparatus achieved by using light polarized as in an embodiment of the present invention, given in reference to the drawings.

Figure 1:
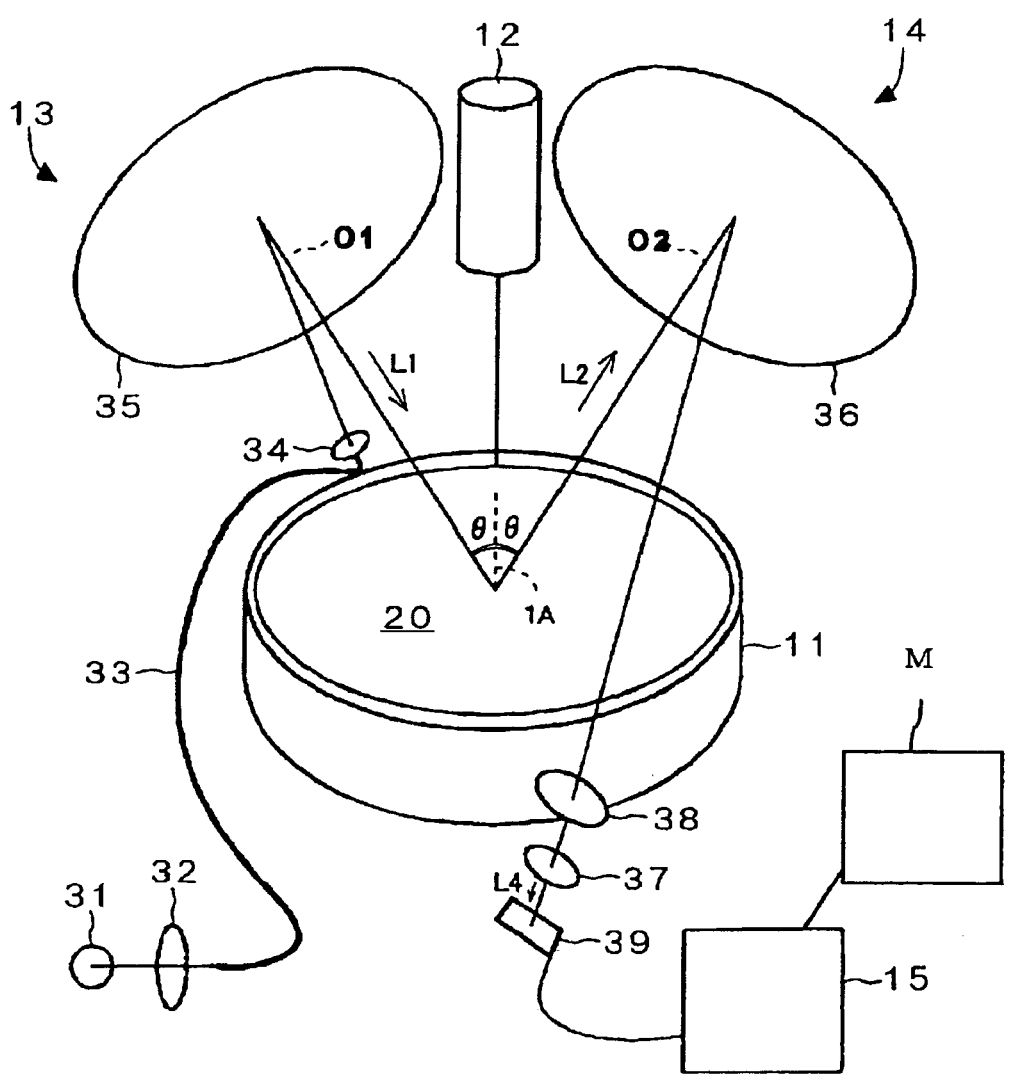
FIG. 1 shows the overall structure of the surface inspection apparatus 30.

A surface inspection apparatus 30 achieved in the embodiment comprises a stage 11 that supports a semiconductor wafer 20, i.e., a test substrate, an alignment system 12, an illuminating system 13, a light-receiving system 14 and an image processing device 15, as shown in FIG. 1. The surface inspection apparatus 30 automatically executes an inspection of the surface of the semiconductor wafer 20 during a process of manufacturing a semiconductor circuit element. After the film at the uppermost layer is exposed and developed, the semiconductor wafer 20 is transferred from a wafer cassette or a developing device (not shown) by a transfer system (not shown) and is set on the stage 11 which then holds it fast.

Figure 2:
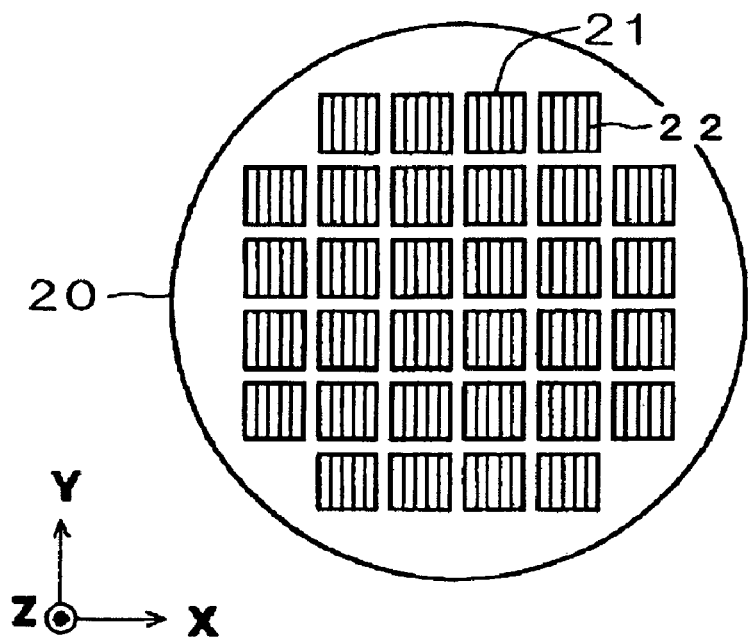
FIG. 2 presents an external view of the surface of the semiconductor wafer 20.
Figure 3:
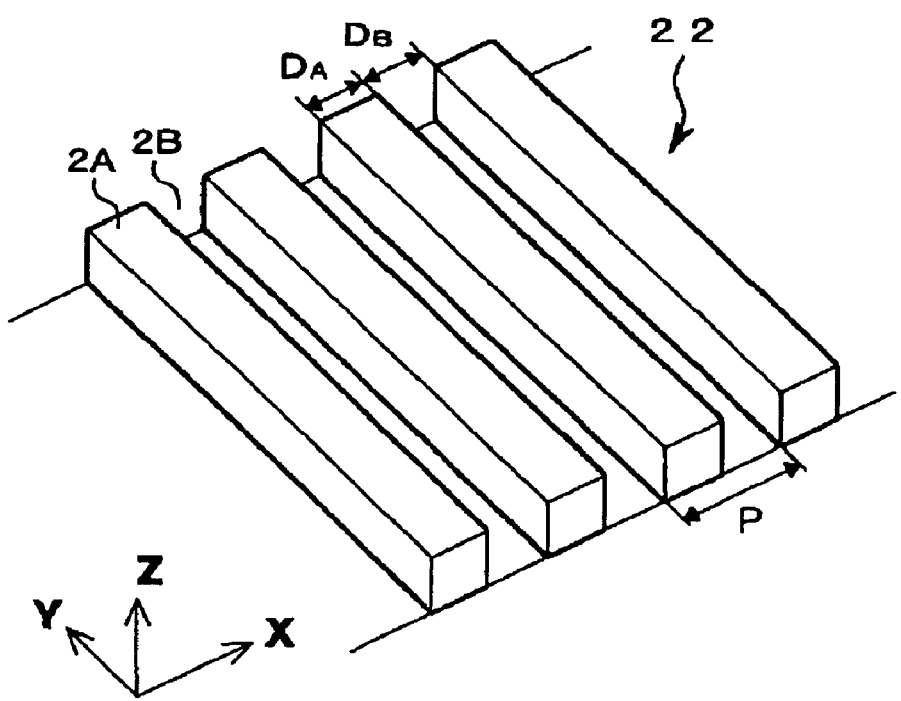
FIG. 3 is a perspective illustrating the structure of a repetitive pattern 22 with recesses and projections.

As shown in FIG. 2, a plurality of chip areas 21 are arrayed along an X direction and a Y direction at the surface of the semiconductor wafer 20 with a repetitive pattern 22 formed within each chip area 21. The repetitive pattern 22 is a resist pattern (e.g., a wiring pattern) having a plurality of line portions 2A arrayed with a constant pitch P along the direction in which their short sides extend (along the X direction), as shown in FIG. 3. Space portions 2B are present between adjacent line portions 2A. The direction along which the line portions 2A are arrayed (the X direction) is referred to as "the repetitive direction of the repetitive pattern 22".

The design value of the line width $D_A$ of the line portions 2A in the repetitive pattern 22 is ½ of the pitch P. If the repetitive pattern 22 is formed exactly as designed, the line width $D_A$ of the line portions 2A and the width $D_B$ of the space portions 2B are equal to each other and the volume ratio of the line portions 2A and the space portions 2B are roughly 1:1. If, on the other hand, the exposure focus does not achieve the correct value while forming the repetitive pattern 22, the line width $D_A$ of the line portions 2A deviates from the design value and the line width $D_A$ and the width $D_B$ of the space portions 2B do not match each other although the pitch P remains unchanged. As a result, the volume ratio of the line portions 2A and the space portions 2B, too, deviates from approximately 1:1.

The surface inspection apparatus 30 achieved in the embodiment inspects the repetitive pattern 22 for defects by checking the change in the volume ratio of the line portions 2A and the space portions 2B in the repetitive pattern 22 described above. For purposes of simplification, the explanation is given by assuming that the ideal volume ratio (design value) is 1:1. The change in the volume ratio, caused by a deviation of the exposure focus from the correct value, manifests in individual shot areas of the semiconductor wafer 20. It is to be noted that the volume ratio may be rephrased as an areal ratio of sections.

It is also assumed that the pitch P of the repetitive pattern 22 is small enough relative to the wavelength of illuminating light (to be detailed later) irradiated on the repetitive pattern 22. Thus, no diffraction light is generated from the repetitive pattern 22, and the repetitive pattern 22 cannot be inspected for defects with diffraction light. The principle of the defect inspection executed in the embodiment is to be explained below in sequence, together with the structure (see FIG. 1) adopted in the surface inspection apparatus 30.

The stage 11 of the surface inspection apparatus 30 holds fast the semiconductor wafer 20 placed on the top surface thereof through, for instance, vacuum suction. In addition, the stage 11 is allowed to rotate around an axis extending along a normal line 1A at the center of the top surface. With this rotary mechanism, the repetitive direction (the X direction in FIGS. 2 and 3) of the repetitive pattern 22 at the semiconductor wafer 20 can be rotated within the surface of the semiconductor wafer 20. It is to be noted that the top surface of the stage 11 is level and the stage 11 does not have a tilt mechanism. Thus, the semiconductor wafer 20 can be held in a level state at all times.

While the stage 11 rotates, the alignment system 12 detects the position of an outer contour reference (e.g., a notch) present at the outer edge of the semiconductor wafer 20 along the rotating direction by illuminating the outer edge of the semi conductor wafer 20 and stops the stage 11 at a specific position. As a result, the repetitive direction (the X direction in FIGS. 2 and 3) of the repetitive pattern 22 at the semiconductor wafer 20 can be set at an angle of 45° relative to a plane of incidence 3A (see FIG. 4) of the illuminating light to be detailed later.

The illuminating system 13, which is a decentered optical system comprising a light source 31, a wavelength selection filter 32, a light guide fiber 33, a polarization plate 34 and a concave reflecting mirror 35, illuminates the repetitive pattern 22 at the semiconductor wafer 20 placed on the stage 11 with linearly polarized light L1. This linearly polarized light L1 is the illuminating light for the repetitive pattern 22. The linearly polarized light L1 is irradiated over the entire surface of the semiconductor wafer 20.

Figure 4:
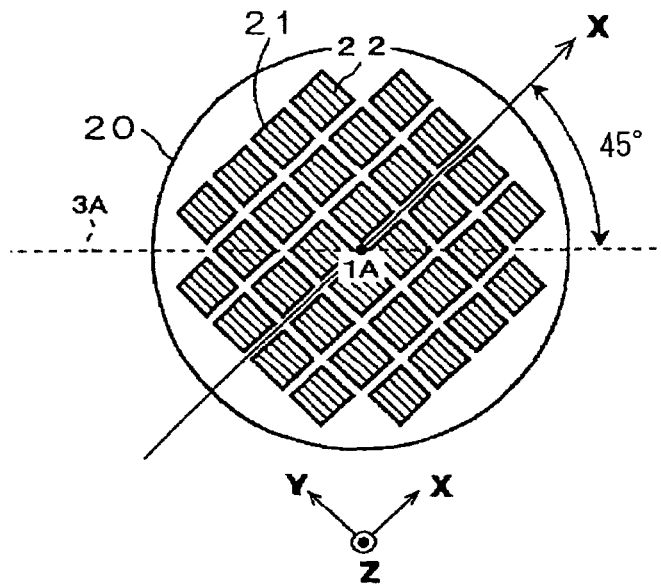
FIG. 4 illustrates how the repetitive direction (the X direction) of the repetitive patterns 22 is set at a tilt relative to the plane of incidence (3A) with respect to the linearly polarized light L1.

The direction in which the linearly polarized light L1 advances (the direction in which the principle ray of the linearly polarized light L1 advances to reach an arbitrary point on the surface of the semiconductor wafer 20) is substantially parallel to an optical axis O1 of the concave reflecting mirror 35. The optical axis O1 extends to pass through the center of the stage 11 is set at a tilt with a predetermined angle θ relative to the normal line 1A of the stage 11. A plane containing the advancing direction of the linearly polarized light L1 and ranging parallel to the normal line 1A of the stage 11 is the plane of incidence of the linearly polarized light L1. The plane of incidence 3A in FIG. 4 is the plane of incidence at the center of the semiconductor wafer 20.

Figure 5:
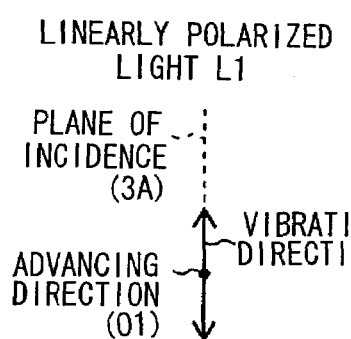
FIGS. 5A to 5C illustrate the directions along which the linearly polarized light L1 and the elliptically polarized light L2 vibrate.
Figure 5:
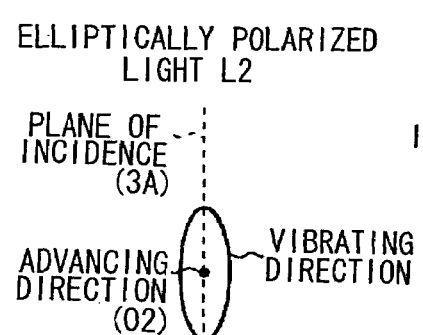
Figure 5:
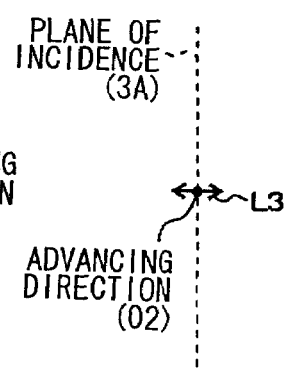

In addition, the explanation is given by assuming that the linearly polarized light L1 is, for instance, p-polarized light. In other words, a plane containing the advancing direction of the linearly polarized light L1 and the direction of the electric vector vibration (the plane of vibration of the linearly polarized light L1) is contained in the plane of incidence (3A) of the linearly polarized light L1, as shown in FIG. 5A. The plane of vibration of the linearly polarized light L1 is defined by the transmission axis of the polarization plate 34 disposed at the stage preceding the concave reflecting mirror 35.

It is to be noted that the light source 31 in the illuminating system 13 is an inexpensive discharge-type light source such as a metal halide lamp or a mercury lamp. A bright line spectrum with a predetermined wavelength in the light emitted from the light source 31 is selectively allowed to be transmitted through the wavelength selection filter 32. The light from the wavelength selection filter 32 is then transmitted through the light guide fiber 33. The polarization plate 34 is disposed near the emission end of the light guide fiber 33, with its transmission axis set with a specific azimuth to convert the light from the light guide fiber 33 to linearly polarized light in correspondence to the transmission axis. The concave reflecting mirror 35 reflects light on the inner side of a spherical surface, is disposed so that its front-side focal point substantially matches the emission end of the light guide fiber 33 and its rear-side focal point substantially matches the surface of the semiconductor wafer 20, and guides the light from the polarization plate 34 to the surface of the semiconductor wafer 20. The illuminating system 13 is an optical system achieving telecentricity relative to the semiconductor wafer 20.

In the illuminating system 13 described above, the light emitted from the light source 31 becomes the linearly polarized light L1 (see FIG. 5A), which is p-polarized light, via the wavelength selection filter 32, the light guide fiber 33, the polarization plate 34 and the concave reflecting mirror 35, and this linearly polarized light L1 then enters the entire surface of the semiconductor wafer 20. The angles of incidence of the linearly polarized light L1 at various points of the semiconductor wafer 20 are equal to one another and are equivalent to the angle θ formed by the optical axis O1 and the normal line 1A.

Since the linearly polarized light L1 entering the semiconductor wafer 20 is p-polarized light (see FIG. 5A), the angle formed by the direction along which the plane of vibration of the linearly polarized light L1 ranges (the V direction in FIG. 6) and the repetitive direction (the X direction) of the repetitive pattern 22 at the surface of the semiconductor wafer 20 is set to 45° if the repetitive direction (the X direction) of the repetitive pattern 22 at the semiconductor wafer 20 is set with an angle of 45° relative to the plane of incidence (3A) of the linearly polarized light L1, as shown in FIG. 4.

In other words, the linearly polarized light L1 enters the repetitive pattern 22 so as to intersect the repetitive pattern 22 diagonally, with the direction of the plane of vibration (the V direction in FIG. 6) at the surface of the semiconductor wafer 20 tilted with a 45° angle relative to the repetitive direction (the X direction) of the repetitive pattern 22.

Figure 6:
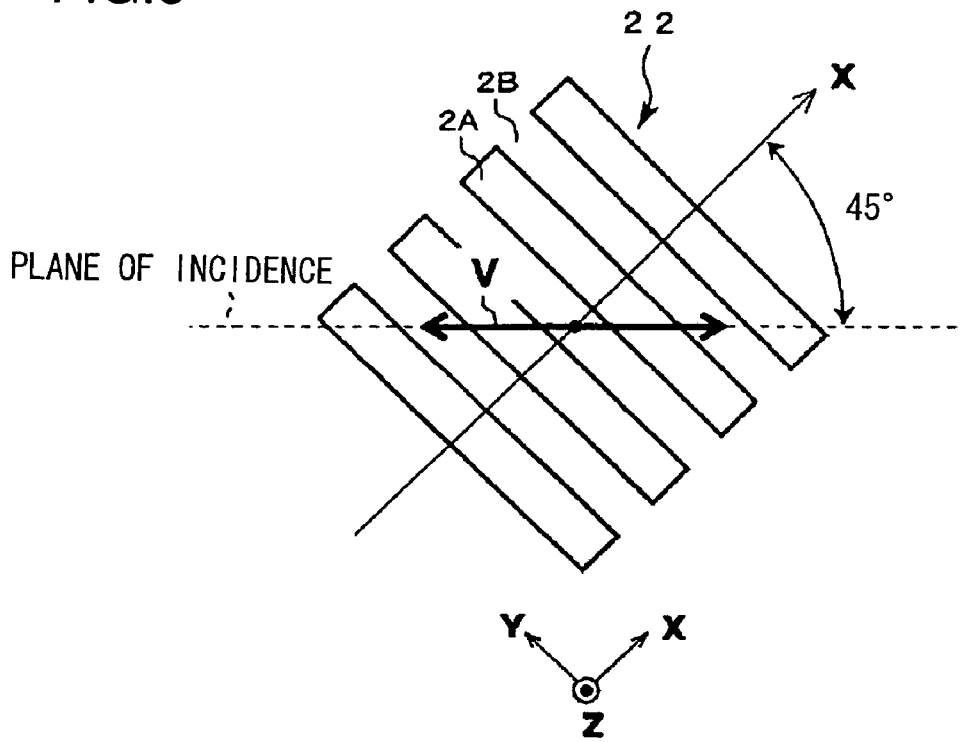
FIG. 6 illustrates how the repetitive direction (the X direction) of a repetitive pattern 22 is set at a tilt relative to the direction (the V direction) along which the plane of vibration of the linearly polarized light L1 ranges.

The angle formed with the linearly polarized light L1 and the repetitive pattern 22 remains constant over the entire surface of the semiconductor wafer 20. It is to be noted that the 45° angle formed by the linearly polarized light L1 and the repetitive pattern 22 may instead be expressed as an angle of 135°, 225° or 315°. In addition, the angle formed with the direction (the V direction) of the plane of vibration and the repetitive direction (the X direction) is set to 45°, as shown in FIG. 6, so as to maximize the sensitivity of the inspection executed to detect defects in the repetitive pattern.

As the repetitive pattern 22 is illuminated with the linearly polarized light L1 described above, elliptically polarized light L2 is generated along the direction of regular reflection from the repetitive pattern 22 (see FIG. 1 and FIG. 5B). The direction along which the elliptically polarized light L2 advances matches the direction of the regular reflection. The direction of the regular reflection is contained within the plane of incidence (3A) of the linearly polarized light L1 and extends at an angle θ (an angle equal to the angle of incidence θ of the linearly polarized light L1) relative to the normal line 1A of the stage 11. It is to be noted that since the pitch P at the repetitive pattern 22 is small enough relative to the illuminating light wavelength, no diffraction light is generated from the repetitive pattern 22.

Figure 7:
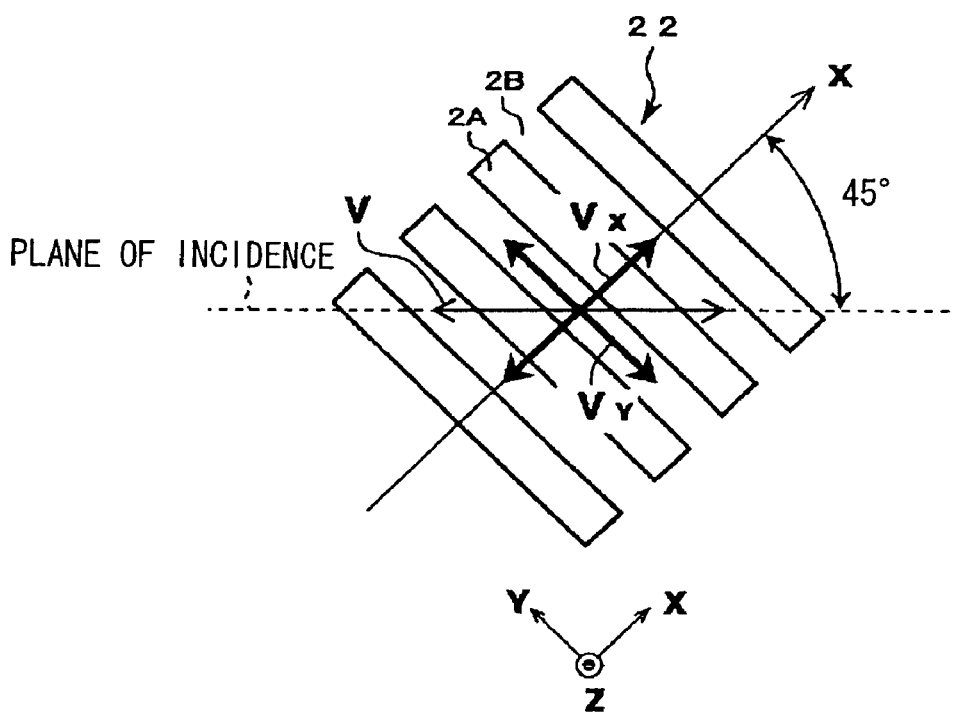
FIG. 7 illustrates how the light is split into a polarization component Vx parallel to the repetitive direction (the X direction) and a polarization component Vy perpendicular to the repetitive direction.

Now, a brief explanation is given on how the polarization of the linearly polarized light L1 becomes elliptical at the repetitive pattern 22 and the elliptically polarized light L2 is generated from the repetitive pattern 22. After the linearly polarized light L1 enters the repetitive pattern 22, the direction of the plane of vibration (the V direction in FIG. 6) is split into two polarization components Vx and Vy, as shown in FIG. 7. One of the polarization components, i.e., the polarization component Vx, is a component parallel to the repetitive direction (the X action). The other polarization component Vy is a component perpendicular to the repetitive direction (the X direction). The two polarization components Vx and Vy undergo different changes in amplitude and different changes in phase, independently of each other. They undergo different changes in amplitude and phase since they have different complex reflectances (i.e., complex amplitude reflectances) due to the anisotropy of the repetitive pattern 22, and the term "form birefringence" is used to refer to this phenomenon. As a result, the amplitude and phase of the reflected light with the polarization component Vx and the amplitude and phase of the reflected light with the polarization component Vy are different from each other, and the elliptically polarized light L2 is achieved as reflected light which is a composition of these (see FIG. 5B).

In addition, the extent of the ellipticity caused by the anisotropy of the repetitive pattern 22 may be considered to be represented by a polarization component L3 (see FIG. 5C) in the elliptically polarized light L2 in FIG. 5B, which is perpendicular to the plane of vibration (which matches the plane of incidence (3A)) of the linearly polarized light L1 in FIG. 5A. The size of the polarization component L3 is dependent on the material constituting the repetitive pattern 22, the form of the repetitive pattern 22 and also the angle formed by the direction (the V direction) of the plane of vibration and the direction (the X direction) of repetition shown in FIG. 6. For this reason, when the angle formed by the V direction and the X direction is sustained at a constant value (e.g., 45°), a change in the form of the repetitive pattern 22 results in a change in the extent of the ellipticity (the size of the polarization component L3) even if the material constituting the repetitive pattern 22 remains the same.

Figure 8:
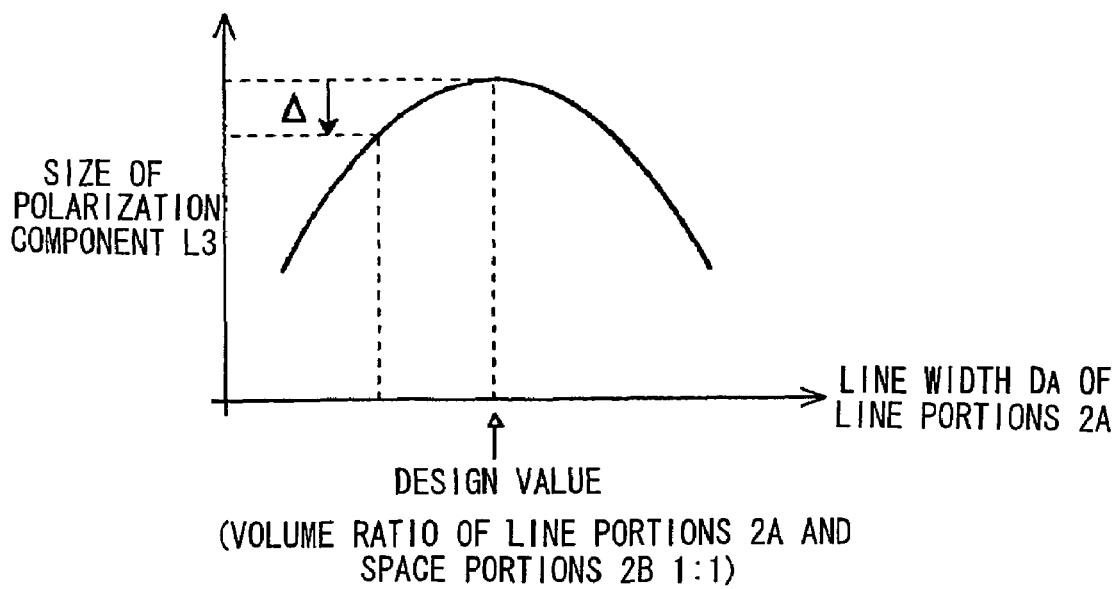
FIG. 8 illustrates the relationship between the size of the polarization component L3 and the line width Da of the lines 2A in the repetitive pattern 22.

The relationship between the form of the repetitive pattern 22 and the size of the polarization component L3 is now explained. As shown in FIG. 3, the repetitive pattern 22 has recesses and projections constituted with the space portions 2B and the line portions 2A alternately arrayed along the X direction, and as long as it is formed with the correct exposure focus achieving specific design values, the linewidth $D_A$ of the line portions 2A and the line width $D_B$ of the space portions 2B are equal to each other with the volume ratio of the line portions 2A and the space portions 2B at approximately 1:1. The size of the polarization component L3 is at its largest when the repetitive pattern 22 achieves this ideal form. If, on the other hand, the exposure focus deviates from the correct value, the line width $D_A$ of the line portions 2A and the line width $D_B$ of the space portions 2B do not match and the volume ratio of the line portions 2A and the space portions 2B deviates from approximately 1:1. The size of the polarization component L3 in such a situation is smaller than the quantity achieved in conjunction with the ideal form. FIG. 8 shows the change in the size of the polarization component L3. The line width $D_A$ of the line portions 2A is indicated along the horizontal axis in FIG. 8.

As the repetitive pattern 22 is illuminated with the linearly polarized light L1 with the direction (the V direction) of the plane of vibration set at a tilt having a 45° angle relative to the repetitive direction (the X direction) of the repetitive pattern 22, as shown in FIG. 6, the extent of the ellipsization (the size of the polarization component L3 in FIG. 5C) through which the elliptically polarized light L2 is generated along the direction of the regular reflection (see FIGS. 1 and 5B) is determined in correspondence to the form of the repetitive pattern 22 (the volume ratio of the line portions 2A and the space portions 2B) (see FIG. 8). The direction along which the elliptically polarized light L2 advances is contained within the plane of incidence (3A) of the linearly polarized light L1 and the advancing direction is set at a tilt having an angle θ (equal to the angle of incidence θ of the linearly polarized light L1) relative to the normal line 1A of the stage 11.

Next, the light-receiving system 14 is explained. As shown in FIG. 1, the light-receiving system 14 is a decentered optical system constituted with a concave reflecting mirror 36, an image forming lens 37, a polarization plate 38 and an image-capturing element 39.

The concave reflecting mirror 36 is similar to the concave reflecting mirror 35 in the illuminating system described earlier, with its optical axis O2 extending to pass through the center of the stage 11 and set at a tilt with an angle θ relative to the normal line 1A at the stage 11. As a result, the elliptically polarized light L2 from the repetitive pattern 22 advances along the optical axis O2 of the concave reflecting mirror 36. The concave reflecting mirror 36 reflects the elliptically polarized light L2, guides the reflected light to the image forming lens 37 and then condenses the light onto the image-capturing surface at the image-capturing element 39 by cooperating with the image forming lens 37.

It is to be noted that the polarization plate 38 is disposed between the image forming lens 37 and the concave reflecting mirror 36. The azimuth of the transmission axis of the polarization plate 38 is set orthogonally to the transmission axis of the polarization plate 34 in the illuminating system 13 described earlier (crossed Nicols state). Accordingly, it is possible to extract only a polarization component L4 in the elliptically polarized light L2, which is equivalent to the polarization component L3 in FIG. 5C by using the polarization plate 38 and the extracted light component can then be guided to the image-capturing element 29. As a result, a reflected image of the semiconductor wafer 20 is formed with the polarization component L4 at the image-capturing surface of the image-capturing element 39.

The image-capturing element 39, which may be a CCD image-capturing element, outputs image signals obtained by executing photoelectric conversion on the reflected image of the semiconductor wafer 20, which is formed at the image-capturing surface, to the image processing device 15. The level of brightness (darkness) of the reflected image of the semiconductor wafer 20 is substantially in proportion to the light intensity of the polarization component L4 (the size of the polarization component L3 in FIG. 5C) and changes in correspondence to the form of the repetitive pattern 22 (the volume ratio of the line portions 2A and the space portions 2B) (see FIG. 8). When the repetitive pattern 22 has to have the ideal form (the volume ratio at 1:1), the reflected image of the semiconductor wafer 2 is at its lightest. It is to be noted that the reflected image of the semiconductor wafer 20 manifests a specific level of brightness/darkness in each shot area.

Based upon the image signals output from the image-capturing element 39, the image processing device 15 takes in the reflected image of the semiconductor wafer 20. It is to be noted that a reflected image of a desirable wafer product is stored in memory at the image processing device 15 in advance to be used for purposes of comparison. The "desirable wafer product" refers to a wafer having repetitive patterns 22 with the ideal form (with the volume ratio at 1:1) over the entire surface. The brightness information with regard to the reflected image of the desirable wafer product is assumed to indicate the highest brightness value.

Accordingly, the image processing device 15 having taken in the reflected image of the semiconductor wafer 20, i.e., the test substrate, compares its brightness information with the brightness information of the reflected image of the desirable wafer product. Then, based upon the extent by which the brightness value is lower at a dark point in the reflected image of the semiconductor wafer 20 (proportional to the reduction extent Δ in FIG. 8), a defect (a change in the volume ratio of the line portions 2A and the space portions 2B) in the repetitive pattern 22 is detected. For instance, if the extent of the reduction in the brightness value is greater than a predetermined threshold value (allowable value), it may be judged that there is a "defect", whereas if the extent is less than the threshold value, the repetitive pattern may be judged to be "normal".

It is to be noted that instead of storing in memory in advance the reflected image of a desirable wafer product at the image processing device 15 as described above, it may store in memory in advance data indicating the wafer shot area array and a threshold value for the brightness value.

In this case, the position of each shot area in the reflected image of the wafer having been taken in can be ascertained based upon the shot area array data, and accordingly, the brightness value for each shot area can be determined. Then, by comparing the brightness value with the threshold value stored in memory, a defect in the pattern can be detected. Any shot area with a brightness value smaller than the threshold value should be judged to be defective.

As described above, the linearly polarized light L1 is used to illuminate the repetitive pattern 22 with the direction (the V direction) of the plane of vibration tilted relative to the repetitive direction (the X direction) of the repetitive pattern 22 as shown in FIG. 6 and any defect in the repetitive pattern 22 is detected based upon the light intensity of the polarization component L4 (the size of the polarization component L3 in FIG. 5C) in the elliptically polarized light L2 generated along the direction of the regular reflection in the surface inspection apparatus 30. As a result, even when the pitch P of the repetitive pattern 22 is considerably smaller than the illuminating light wavelength, the defect inspection can be executed with a high level of reliability. In other words, a pattern repeating with a very small pitch can be inspected without having to reduce the wavelength of the linearly polarized light L1 used to illuminate the pattern.

In addition, the surface inspection apparatus 30, in which the angle formed with the direction (the V direction) of the plane of vibration and the repetitive direction (the X direction) is set to 45°, as shown in FIG. 6, is capable of detecting the extent to which the brightness value of the reflected image of the semiconductor wafer 20 is greatly reduced (proportional to the reduction extent Δ in FIG. 8) and thus executing the defect inspection of the repetitive pattern 22 with high sensitivity.

The surface inspection apparatus 30 is capable of executing a defect inspection of a repetitive pattern 22 with its pitch P set substantially equal to the illuminating light wavelength or greater than the illuminating light wavelength with comparable effectiveness as well as of a repetitive pattern 22 with a pitch P set significantly smaller than the illuminating light wavelength. In other words, it is capable of executing a reliable defect inspection of a repetitive pattern 22 with any pitch P, since the ellipticity of the linearly polarized light L1 at the repetitive pattern 22 is induced dependent on the volume ratio of the line portions 2A and the space portions 2B in the repetitive pattern 22 and not dependent on the pitch P of the repetitive pattern 22.

Figure 9:
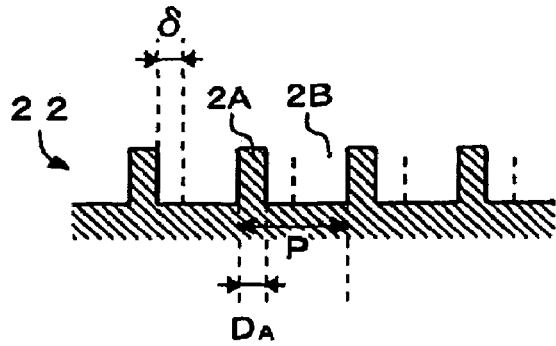
FIGS. 9A and 9B present an example of repetitive patterns 22 with different pitches P, having volume ratios of the lines 2A to the spaces 2B equal to each other.
Figure 9:
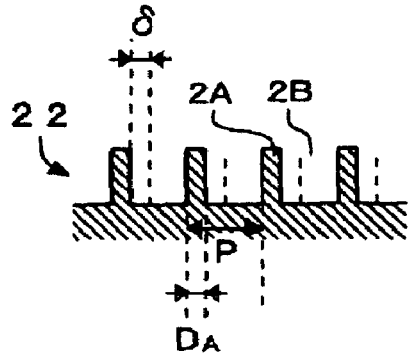

Furthermore, as long as repetitive patterns 22 have volume ratios of the line portions 2A and the space portions 2B equal to each other, the brightness values in the reflected image become reduced by the same extent (proportional to the reduction extent Δ in FIG. 8) to equal extent at the surface inspection apparatus 30. For this reason, volume ratio changes occurring to equal degrees can be detected with the same level of sensitivity, regardless of the pitches P of the repetitive patterns 22. For instance, when the volume ratios of the line portions 2A and the space portions 2B in repetitive patterns with varying pitches P are equal to each other, as in the case of repetitive patterns 22 shown in FIGS. 9A and 9B, they can be inspected for defects with the same level of sensitivity. In addition, as a comparison of FIGS. 9A and 9B indicates, a very subtle change in the form (the extent of deviation δ of the line width $D_A$ of the line portions 2A from the design value) can be detected with a higher degree of reliability when the pitch P is smaller.

Since the inspection can be executed in the surface inspection by keeping the semiconductor wafer 20 in a level state (without having to execute a tilt adjustment for the stage as required in the related art) when inspecting a repetitive pattern 22 with a different pitch P, the length of time required as a preparatory period leading up to the start of the actual defect inspection (i.e., leading up to the actual intake of the reflected image of the semiconductor wafer 20) can be reduced significantly to improve the work efficiency.

Also, since the stage 11 does not include a tilt mechanism, the apparatus structure of the surface inspection apparatus 30 is simplified. In addition, since an inexpensive discharge-type light source can be used as the light source 31 of the illuminating system 13, a simpler structure is achieved for the entire surface inspection apparatus 30 at low cost.

Figure 10:
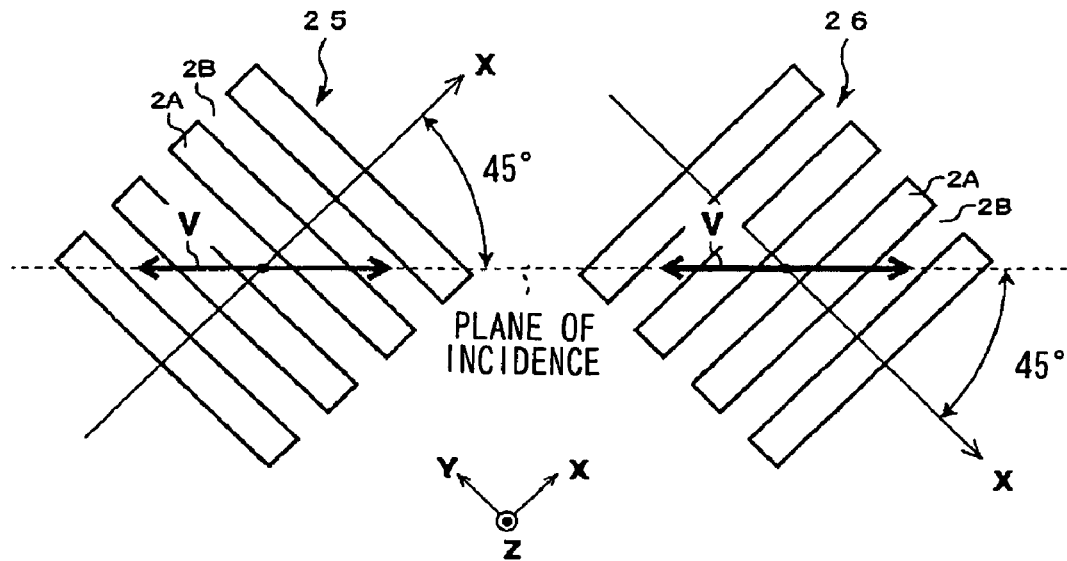
FIG. 10 shows repetitive patterns 25 and 26 reiterating along different directions from each other.

Even when the semiconductor wafer 20 includes a plurality of types of repetitive patterns with varying pitches P and varying repetitive directions (X directions) formed at the surface thereof, the defect inspection for all the repetitive patterns can be executed with ease simply by taking in the reflected image of the entire surface of the semiconductor wafer 20 in a batch and then checking the extent to which the brightness values are lowered at the individual positions with the surface inspection apparatus 30. Repetitive patterns with different repetitive directions may be a repetitive pattern 25 that reiterates along the 0° direction and a repetitive pattern 26 that reiterates along the 90° direction shown in FIG. 10. These repetitive patterns 25 and 26 reiterate in directions (the X directions) offset from each other by 90°. However, the angles formed by their repetitive directions (the X directions) and the direction (the V direction) of the plane of vibration of the linearly polarized light L1 are both 45°.

Moreover, the surface inspection apparatus 30, in which the linearly polarized light L1 is made to diagonally enter the surface of the semiconductor wafer 20 (see FIG. 1), is able to obtain defect information related to asymmetry of the edges (e.g., the directionality of the deformation in the edge form) at the line portions 2A in the repetitive pattern 22 as well. In order to obtain such defect information, the repetitive direction (the X direction) of the repetitive pattern 22 at the semiconductor wafer 20 is rotated by 180° via the stage 11, the reflected images of the semiconductor wafer 20 before and after the rotation are taken in and the difference in the brightness at a given point is ascertained.

Figure 11A:
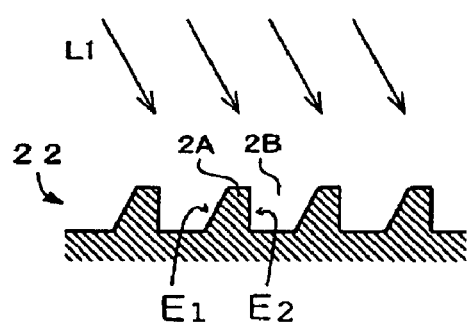
FIGS. 11A and 11B show how the linearly polarized light L1 enters a repetitive pattern 22 with asymmetrical edges.
Figure 11B:
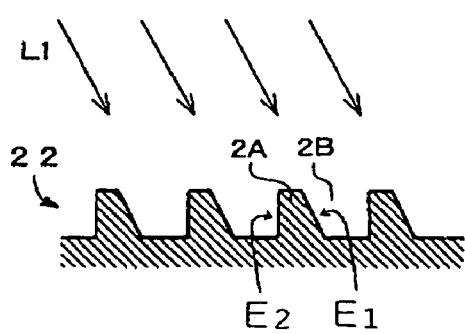

FIGS. 11A and 11B show the relationship between a repetitive pattern 22 manifesting asymmetry in the edge form and the direction along which the linearly polarized light L1 enters. FIG. 11A, for instance, shows the state prior to the 180° rotation, with the illuminating light entering from the side towards the deformed edge (E1) of the edges E1 and E2 at each line portion 2A. FIG. 11B shows the state following the 180° rotation, with the illuminating light entering from the side towards a well-formed edge (E2) of the two edges E1 and E2. The brightness values in the reflected images acquired in the different states each reflect the form of the edge E1 or E2 on the side toward which the illuminating light enters. In this example, the reflected image acquired in the state shown in FIG. 11A indicates a greater brightness value. Accordingly, by checking the difference in the brightness between the reflected images acquired before and after the 180° rotation, any asymmetry in the edge forms of the line portions 2A can be detected. Alternatively, the defect inspection may be executed by combining the reflected images acquired before and after the 180° rotation.

To be more precise, when the linearly polarized light L1 is made to diagonally enter the surface of the semiconductor wafer 20 (see FIG. 1, the angle of incidence θ) the elliptically polarized light L2 (see FIG. 5B) generated from the repetitive pattern 22 rotates slightly around an axis extending along its advancing direction. For this reason, it is desirable to fine-adjust the azimuth of the transmission axis of the polarization plate 38 in the light-receiving system 14 by taking into consideration the angle of this rotation. The azimuths of the transmission axes of the two polarization plates 34 and 38 after the fine-adjustment are such that the angle formed by the transmission axes is no longer exactly 90°. However, this angle can still be considered to be within the broad range of being "vertical" (or "orthogonal"), achieving a crossed Nicols state. By fine-adjusting the azimuth of the transmission axis of the polarization plate 38, the accuracy of the inspection can be improved. The fine-adjustment may be performed by, for instance, acquiring an image while reflecting the linearly polarized light L1 at a surface where no repetitive pattern is present and then by rotating the azimuth of the transmission axis of the polarization plate 38 until the image achieves the smallest brightness value.

While the linearly polarized light L1 is p-polarized light in the example explained above, the present invention is not limited to this example. The linearly polarized light may be s-polarized light instead of p-polarized light. S-polarized light is linearly polarized light with its plane of vibration ranging perpendicular to the plane of incidence. Thus, when the repetitive direction (the X direction) of the repetitive pattern 22 at the semiconductor wafer 20 is set at a 45° angle relative to the plane of incidence (3A) of the s-polarized light, i.e., the linearly polarized light L1, the angle formed by the direction of the plane of vibration of the s-polarized light and the repetitive direction (the X direction) of the repetitive pattern 22, too, is set to 45° as shown in FIG. 4. It is to be noted that the use of the p-polarized light is more suitable for obtaining defect information related to the edge forms of the line portions 2A in the repetitive pattern 22. The s-polarized light is more suited for improving the SN ratio by obtaining defect information related to defects at the surface of the semiconductor wafer 20 with a high degree of efficiency.

In addition, instead of p-polarized light or s-polarized light, linearly polarized light with its plane of vibration tilted with any angle relative to the plane of incidence may be used. In such a case, it is desirable to set the repetitive direction (the X direction) of the repetitive pattern 22 at an angle other than 45° relative to the plane of incidence of the linearly polarized light L1 and set the angle formed by the direction of the plane of vibration of the linearly polarized light L1 and the repetitive direction (the X direction) of the repetitive pattern 22 at the surface of the semiconductor wafer 20 to 45°.

Figure 12:
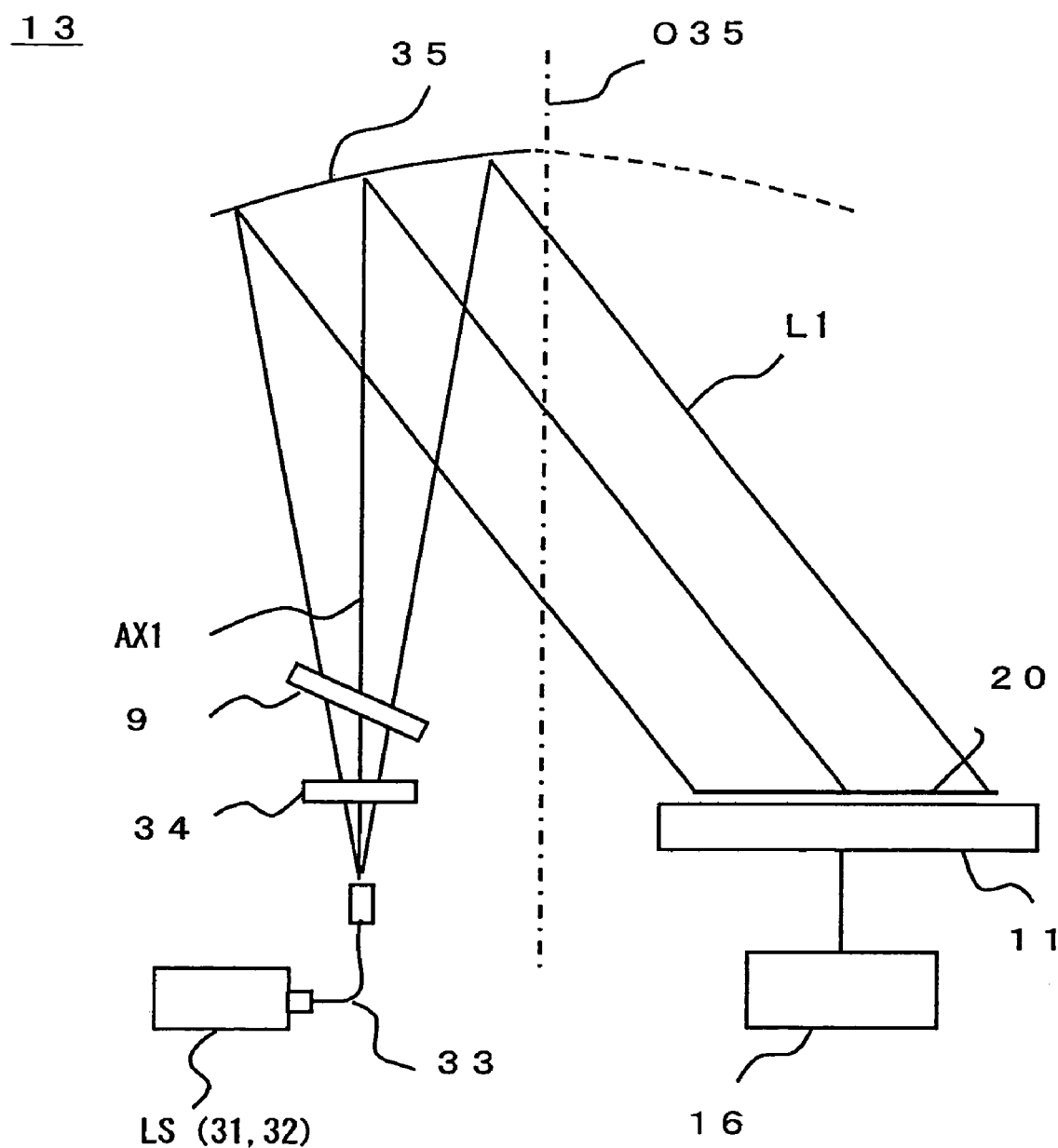
FIG. 12 shows the overall structure adopted in the surface inspection apparatus achieved in a first embodiment.

FIG. 12 shows the illuminating optical system 13 used in the embodiment. Inside a lamp housing LS, the light source 31 such as a halogen lamp, a metal halide lamp or a mercury lamp (not shown), the wavelength selection filter 32, an ND filter used in light quantity adjustment and the like are disposed as internal components, and only the light with a specific wavelength is extracted as illuminating light L1 and enters the light guide fiber 33. The illuminating optical system 13 comprises the light guide fiber 33, the polarization plate 34, the polarization correcting plate 9 and the concave reflecting mirror 35. The illuminating light L1, which is a divergent light flux emitted from the light guide fiber 33, is converted to substantially parallel light at the concave reflecting mirror 35 assuming a spherical form and illuminates the wafer 20 set on the stage 11. The polarization plate 34 is disposed in the vicinity of the emission area of the light guide fiber 33 to convert the illuminating light L1 emitted from the light guide fiber 33 to linearly polarized light. The light having been converted to linearly polarized light at the polarization plate 34 travels through the polarization correcting plate 9 to be detailed later, and is collimated at the concave reflecting mirror 35. The wafer 20 is illuminated with the collimated linearly polarized light. Since it is highly advantageous to acquire an image of the entire wafer surface in a batch for purposes of improved throughput, the light flux from the light source is expanded and then is collimated at the concave reflecting mirror 35 in the embodiment, as described above, so as to illuminate the entire wafer surface.

The illuminating optical system 13 in the embodiment includes the polarization correcting plate 9 disposed between the polarization plate 34 and the concave reflecting mirror 35. First, let us consider the state of polarization of a light flux having entered and been reflected at the concave reflecting mirror 12 in a structure that does not include a polarization correcting plate.

The optical system in FIG. 12 is a so-called off-axis optical system, in which the illuminating light L1, made to diverge in correspondence to the numerical aperture at the light guide fiber 33, is converted to a specific type of linearly polarized light at the polarization plate 34 as described earlier, and the principal ray AX1 of the divergent light flux enters the concave reflecting mirror 35 at a position offset from the optical axis O35 of the concave reflecting mirror 35. In order to facilitate the explanation, a plane containing the principal ray AX of the linearly polarized light L1 entering the concave reflecting mirror and the perpendicular taken at the point at which the principal ray enters the concave reflecting mirror is defined as a reference plane of incidence A4 of the linearly polarized light L1 entering the concave reflecting mirror. In addition, an axis contained in the reference plane of incidence, which extends parallel to the principal ray and perpendicularly crosses the concave reflecting mirror is defined as the optical axis O35 of the concave reflecting mirror.

As described earlier, the light flux entering the concave reflecting mirror 35 is a divergent light flux. For this reason, the difference manifests between the transmittance of the p component and the transmittance of the s component of the polarized light as indicated in Frenel's formula of reflection, resulting in a rotation of the plane of polarization.

Figure 13:
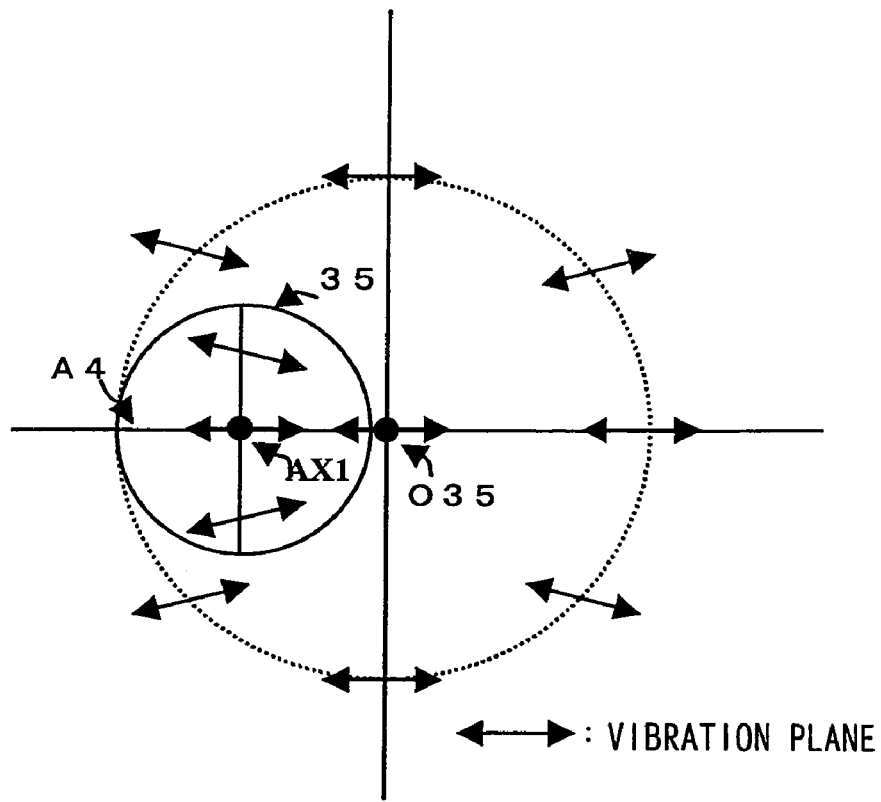
FIG. 13A shows how the polarization rotates at the concave reflecting mirror 35.
FIG. 13B shows how the polarization rotates at the polarization correcting plate 9.
Figure 13:
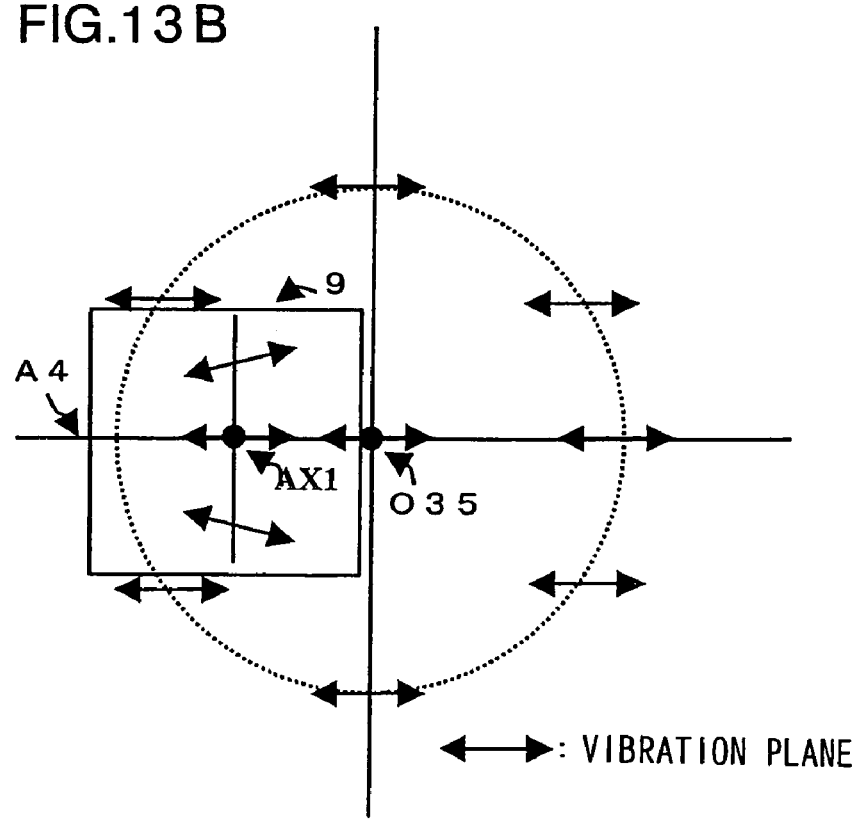

The following is an explanation of the behavior characterizing the rotation of the plane of polarization. Let us consider a situation in which a linearly polarized divergent light flux having a plane of vibration parallel to the reference plane of incidence A4 (p-polarized light) enters the concave reflecting mirror 35. FIGS. 13A and 13B show this state. While FIG. 12 shows the light emitted from the light source entering only over the effective diameter of the concave reflecting mirror 35, FIGS. 13A and 13B show enlargements of the concave reflecting mirror as a circle (indicated with the dotted line) centered around the optical axis O35 and containing the effective diameter of the concave reflecting mirror 35, with an incident light flux having a diameter large enough to illuminate the entire circle. In this situation, while the plane of polarization does not rotate at a portion of the surface of the concave reflecting mirror 35 that intersects the reference plane of incidence A4 and at a portion of the surface of the concave reflecting mirror 35 that intersects a plane containing the optical axis O35 and ranging perpendicular to the reference plane of incidence A4, rotation does occur at the remaining portion of the concave reflecting mirror 35. As shown in FIGS. 13A and 13B, the plane of vibration of the polarized light rotates by achieving line symmetry relative to the reference plane of incidence within the plane of the concave reflecting mirror 35. The rotation of the plane of vibration of the polarized light also achieves line symmetry relative to the plane containing the optical axis O35 and ranging perpendicular to the reference plane of incidence. The polarized light rotates to a greater extent at a position further distanced from the optical axis O35 of the concave reflecting mirror, since the incident light achieves a greater angle of incidence at a position further away from the optical axis of the concave reflecting mirror, i.e., at a position further distanced from the point of vertical incidence.

A divergent light flux entering at a position offset from the optical axis O35 of the concave reflecting mirror 35, (an area 35 encircled by the solid line in FIG. 13A corresponds to the light flux entry area of the concave reflecting mirror 35), has an inclination that achieves the smallest angle of incidence toward the left end of the light flux entering the concave reflecting mirror 35 and the largest angle of incidence toward the right end (the angle of incidence is the angle formed by the incident light and the normal line of the concave reflecting mirror surface), as shown in FIG. 12.

Since the light entering the concave reflecting mirror has varying angles of incidence within the plane (has an inclination) as described above, a slight difference occurs in the rotation of the polarization plane within the plane, which results in inconsistency in the extinction ratio when, for instance, the polarization plate is disposed at a rear stage with a crossed Nicols configuration.

The azimuth angle αr of the polarization of reflected light when linearly polarized light with an azimuth angle αi enters a concave reflecting mirror is expressed as in (1) below $$\tan \alpha r = rs/rp \cdot \exp(i \cdot (\Delta s - \Delta p)) \tan \alpha i \qquad (1)$$
$$= rs/rp \cdot \exp(i \cdot \Delta) \tan \alpha i$$

rp and rs respectively represent the amplitude reflectances of the two components (hereafter referred to as the p component and the s component) which vibrate along directions perpendicular to each other within a plane perpendicular to the light advancing direction, and Δp and Δs respectively represent phase differences attributable to the reflections of the p component and the s component, which are each indicated as a value determined by the complex refractive index at the reflecting surface and the angle of incidence (refer to, for instance, the chapter on metal optics in Principles of Optics III by Max Born and Emil Wolf). The reflecting surface of the concave reflecting mirror is constituted of a metal such as aluminum and the phase differences Δ and the amplitude reflectances rp and rs in expression (1) change in correspondence to the angle of incidence.

In the embodiment, the concave reflecting mirror 35 having the aluminum reflecting surface is the sole optical member disposed between the polarization plate 34 and the wafer 20 and the polarization plane of the light flux reflected at the concave reflecting mirror rotates to a very small extent of a few degrees (a 3° rotation of the polarization plane is equivalent to a phase change of 1/60 of the wavelength λ of the illuminating light).

In addition, since the divergent light flux L1 enters the concave reflecting mirrors 35 at a position off its optical axis as described earlier, symmetrical rotation occur in the linearly polarized light flux having entered the surface of the concave reflecting mirror 35 relative to the plane of incidence A4. The extent of rotation increases as the distance from the optical axis O35 of the concave reflecting mirror 35 increases. Accordingly, the extent of rotation manifests an inclination toward the optical axis O35.

In order to eliminate the inconsistency in the rotation of the polarization plane within the plane of the illuminating light attributable to the very small rotation of the polarization plane distributed with inclinations, the polarization correcting plate 9 is disposed between the polarization plate 34 and the concave reflecting mirror 35 in the embodiment. The polarization correcting plate 9, which is a plane parallel plate constituted of glass, is disposed at an inclination relative to the optical axis AX1 of the illuminating light L1. The following is an explanation of the function of the polarization correcting plate 9.

The light flux L1 having been emitted from the light guide fiber 33 and having been converted to the nearly polarized light at the polarization plate 34 then enters the polarization correcting plate 9. Since the light flux L1 is a divergent light flux and the polarization correcting plate 9 is disposed at a tilt relative to the optical axis AX1, the angle of incidence of the light flux entering the polarization correcting plate 9 manifests an inclination along a section of the light flux.

The azimuth angle of the polarization of the transmitted light in the light flux having entered the polarization correcting plate with an azimuth angle of α'i is expressed as in (2).

$$\tan \alpha i = ts/tp \cdot \exp(i \cdot (\Delta s - \Delta p)) \cdot \tan \alpha' i \quad (2)$$
$$= ts/tp \cdot \exp(i \cdot \Delta) \cdot \tan \alpha' i$$

In the expression above, ts and tp respectively represent the amplitude transmittances of the s component and the p component at the transmission surfaces and $\Delta p$ and $\Delta s$ represent phase differences attributable to the transmission of the s component and the p component respectively. ts, tp, $\Delta p$ and $\Delta s$ are each functions of the refractive index of the glass and the angle of incidence.

At an ideal phase plate, the relationship expressed as $\Delta = 2\delta$ manifests between the phase difference $\Delta$ and the extent of rotation $\delta$ of the polarization plane and it may be assumed that this relationship is substantially satisfied in the embodiment. Thus, the phase difference $\Delta$ between the p component and the s component in the illuminating light L1 having been transmitted through the polarization correcting plate 9 changes in correspondence to the angle of incidence of the incident light to result in rotation of the polarization plane. FIG. 13B shows the rotation of the polarized light induced by the polarization correcting plate 9.

The plane of polarization of the illuminating light L1 illuminating the wafer 20 represents the sum of the extent of rotation of the polarization plane induced at the polarization correcting plate 9 and the extent of rotation of the polarization plane induced at the concave reflecting mirror 35. Accordingly, by disposing the polarization correcting plate 9 with a tilt relative to the optical axis AX1 of the illuminating optical system so as to induce rotation of the polarization plane with an inclination toward the opposite side from the inclination of the rotation of the polarization plane induced at the concave reflecting mirror 35, a uniform extent of rotation is achieved over the polarization plane (i.e., a uniform azimuth angle α can be achieved over the entire plane of the illuminating light flux).

As explained earlier, the linearly polarized light flux having entered the concave reflecting mirror 35 manifests rotation that are symmetrical relative to the plane of incidence A4 with greater extent of rotation increases as the distances from the optical axis O35 of the concave reflecting mirror 35 increase (i.e., manifesting an inclination relative to the optical axis O35 of the concave reflecting mirror). In order to achieve an inclination toward the opposite side relative to this inclination, the polarization correcting plate is disposed with an inclination toward the opposite side from the direction of the inclination of the concave reflecting mirror relative to the light flux, so as to substantially achieve uniformity in the distribution of the extent of rotation of the polarization plane along a section of the light flux reflected at the concave reflecting mirror 35.

Figure 16:
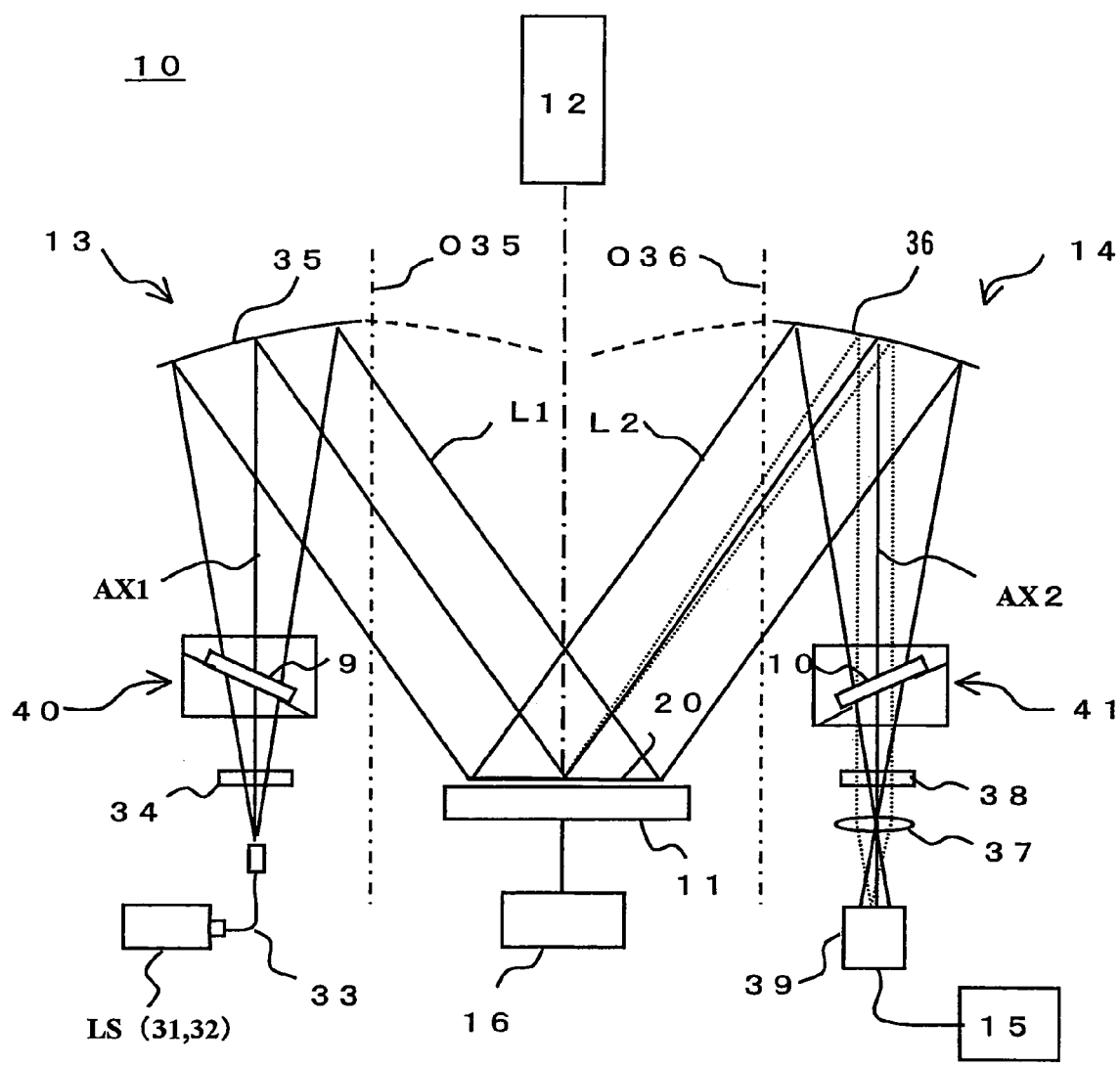
FIG. 16 shows a variation of the surface inspection apparatus achieved in the third embodiment.

It is desirable that a position adjuster 40 capable of setting a desirable angle of inclination and a desirable direction of inclination be disposed at the polarization correcting plate 9, as shown in FIG. 16. The inclusion of the position adjuster in the structure makes it possible to adjust even a slight extent of inconsistency attributable to the apparatus. In addition, by adjusting either of or both of the angle of inclination and the direction of inclination in correspondence to the extent of the change occurring in the extent of rotation of the polarization plane or the change in the distribution thereof induced at the concave reflecting mirror 35 when the illuminating light wavelength is altered at the light source 31 and the wavelength selection filter, the extent to which the phase correction is implemented can be adjusted. Furthermore, a fine adjustment can be executed by reflecting apparatus conditions such as, for instance, the condition of the apparatus adjustment. The position adjustment mechanism actually achieves an adjustment that includes a fine adjustment in the phase difference change range of 1/(several 10 s) of the illuminating wavelength λ.

As described above, the illuminating optical system 13, which includes the polarization correcting plate 9, is capable of correcting the inclination in the extent of rotation of the polarization plane along a section of the light flux at the concave reflecting mirror 12 and thus, illuminating light achieving uniformity in the direction of the rotation of the polarization plane can be irradiated over the entire surface of the wafer.

Figure 15:
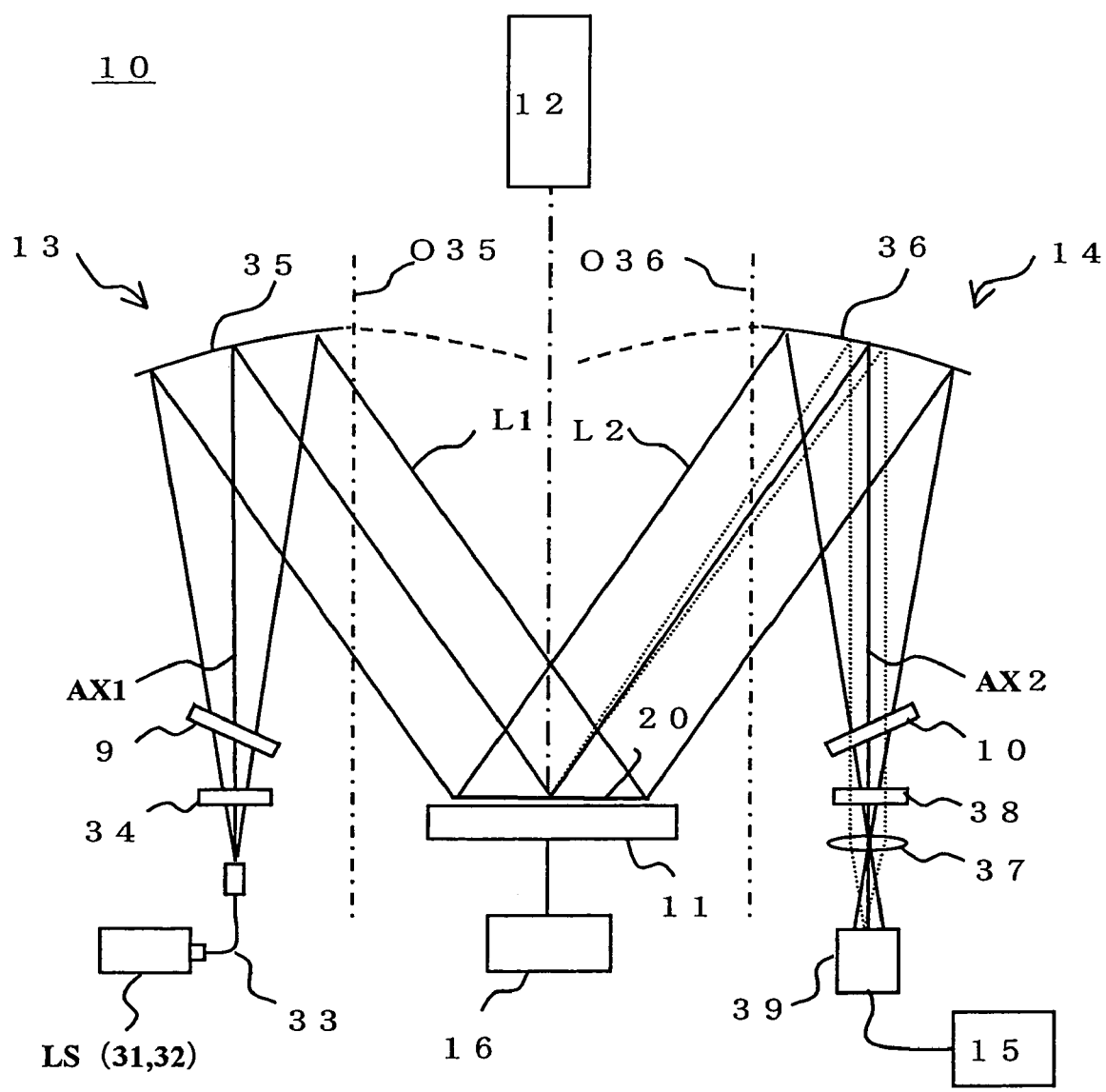
FIG. 15 shows the overall structure adopted in the surface inspection apparatus achieved in a third embodiment.

As explained above, since the concave reflecting mirror 35 is used off axis to convert the divergent light flux to a parallel light flux, the light enters various points of the concave reflecting mirror 35 with varying angles of incidence relative to the normal line (the values of the angles of incidence on the left side and the right side of the concave reflecting mirror 35 in FIG. 15 manifest an inclination) and thus, a tilt occurs with regard to the rotation of the polarization plane. The rotational angles of the polarization planes are very small. In order to achieve uniformity in the distribution of these rotational angles, the polarization correcting plate 9, too, must achieve a phase difference with a very small inclination. As explained earlier, when a light flux enters a glass surface at an angle, the phase difference attributable to the p-polarization and the phase difference attributable to the s-polarization do not match. The embodiment takes advantage of this discrepancy in the phase differences so as to create the required inclination of the phase difference by disposing the plane parallel glass plate at a tilt toward the nonparallel light flux and, as a result, a slight extent of irregularity in the distribution of the rotation of the vibration plane of the polarized light in the optical system using the off axis concave reflecting mirror can be corrected with uniformity. In addition, since the angle of inclination and the direction of inclination of the plane parallel plate are adjustable and the extent of the inclination of the phase difference can be adjusted in the order of 1/(several 10 s) or ⅟₁₀₀ of the wavelength λ, a fine adjustment reflecting conditions of the particular illuminating device in use is enabled.

The embodiment achieves an additional advantage in that since a plane parallel glass plate is used, it remains free of any adverse effect of the machining error (normally manifesting to an extent of approximately 10%) which should be expected to occur at a regular phase plate.

Second Embodiment

Figure 14:
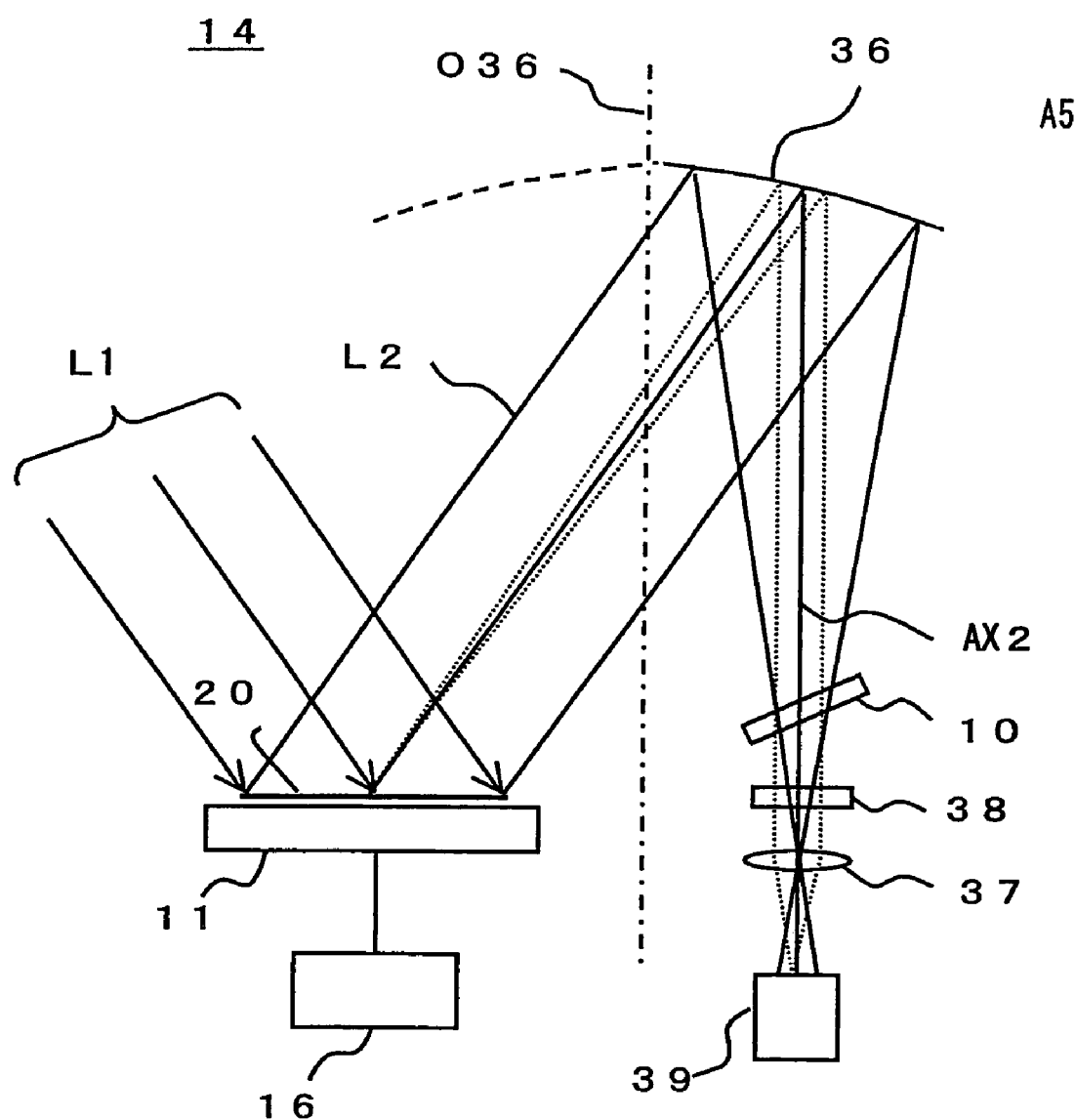
FIG. 14 shows the overall structure adopted in the surface inspection apparatus achieved in a second embodiment.

The second embodiment explained in reference to FIG. 14 features the light-receiving optical system of the surface inspection apparatus. The light-receiving optical system 14 achieved in the embodiment comprises a concave mirror 36 at which light from the wafer 20 enters and is condensed, a polarization correcting plate 10 to be detailed later, the polarization plate 38, a lens 37 and the image-capturing element 39.

The wafer 20 is illuminated with a linearly polarized light flux L1 with uniformity achieved in the extent of rotation of the polarization plane taken along a section of the illuminating light by, for instance, a polarization illuminating optical system having the polarization correcting plate 9, such as that explained in reference to the first embodiment. The wafer is set so that the direction along which the repetitive patterns repeat achieves a 45° angle relative to the plane of vibration of the linearly polarized illuminating light, as has been explained in the description of the principle. Regular reflected light L2 generated from the wafer 20 will have undergone a change in the state of polarization due to form birefringence attributable to the conditions of the repetitive patterns (e.g., the pattern form, the pitch, the forms of the edges, etc.) formed at the wafer surface.

The regular reflected light L2 from the wafer 20 is guided to and condensed at the light-receiving optical system 14 constituted with the concave reflecting mirror 36 and the lens 37, and an image of the wafer 2 is formed on the image-capturing surface of the image-capturing element 39 with the regular reflected light L2. The image-capturing element 39 may be, for instance, a two-dimensional CCD camera.

The polarization plate 38 is disposed between the concave reflecting mirror 36 and the lens 37 so as to allow linearly polarized light orthogonal to the linearly polarized illumination light L1 to be transmitted. A polarization correcting plate 10 is disposed between the polarization plate 38 and the concave reflecting mirror 36.

In the first embodiment, the polarization correcting plate 9 is used to correct the inclination in the extent of rotation of the polarization plane taken along a section of the divergent light flux entering the concave reflecting mirror 35 so as to achieve uniformity among the extent of rotation of the polarization plane. Based upon a principle similar to this, the polarization correcting plate 10 in the light-receiving optical system 14 corrects the inclination of the extent of rotation of the polarization plane taken along a section of convergent light flux departing the concave reflecting mirror 36 after having been reflected at the concave reflecting mirror 36 so as to achieve uniformity in the extent of rotation of polarization plane.

In FIG. 14, since the parallel light flux L2 reflected from the wafer 20 enters the concave reflecting mirror 36 at a position off the optical axis O36 thereof and is subjected to the convergence effect, the light-receiving optical system 14 is achieved as a so-called off-axis optical system.

In order to facilitate the explanation, a plane containing the principal ray AX2 of the linearly polarized light L2 emitted from the concave reflecting mirror 36 and the perpendicular taken at the point at which the principal ray AX2 exits the concave reflecting mirror 36 is defined as a reference plane of incidence A5 of the linearly polarized light L2 exiting the concave reflecting mirror 36, much in the same way that the reference plane of incidence is defined in the first embodiment. In addition, an axis in the reference plane of incidence, which extends parallel to the principal ray and perpendicularly crosses the concave reflecting mirror is defined as the optical axis O36 of the concave reflecting mirror.

The explanation of the first embodiment having been given in reference to FIGS. 13A and 13B also applies to the rotation of the polarization plane occurring in the convergent light flux exiting the concave reflecting mirror 36. Within the plane of the concave reflecting mirror 36, the plane of vibration of polarized light rotates by achieving line symmetry relative to the reference plane of incidence A5. The extent of rotation increases as the distance from the optical axis O36 of the concave reflecting mirror increases, since the convergent light flux L2 exiting the concave reflecting mirror 36 exits the concave reflecting mirror 36 at a position off the optical axis O36 with an inclination that achieves the smallest angle of incidence on the far right end of the light flux exiting the concave reflecting mirror 36 and achieves the largest angle of incidence at the far left of the light flux (the angle of incidence is formed by the incident relative to the normal line taken at the surface of the concave reflecting mirror). The angle of incidence may be rephrased as the angle of emergence or the exit angle here. Since light exiting the concave reflecting mirror has varying angles of emergence within the plane (has an inclination) as described above, a slight difference occurs in the rotation of the polarization plane within the plane, which results in inconsistency in the extinction ratio when, for instance, the polarization plate is disposed in a crossed Nicols configuration.

The polarization correcting plate 10 is constituted with a glass plane parallel plate, as is the polarization correcting plate 9 explained in reference to the first embodiment, and is disposed at an inclination relative to the principal ray AX2 of the regular reflected light L2. Since the regular reflected light L2 is convergent light, the angle of incidence at the polarization correcting plate 10 disposed at an inclination relative to the optical axis AX2 manifests an inclination along a section of the light flux.

Thus, a phase difference between the p component and the s component with an inclination reflecting the angle of incidence can be induced at the polarization correcting plate 10, as at the polarization correcting plate 9. By setting the angle of the polarization correcting plate so that the phase difference between the p component and the s component achieves a distribution with an inclination to the opposite side from the inclination of the distribution of the phase difference between the p component and the s component at a concave reflecting mirror 36, substantial uniformity can be achieved with regard to the rotation of the polarization plane.

It is desirable that a position adjuster 41 capable of setting a desirable angle of inclination and a desirable direction of inclination be disposed at the polarization correcting plate 10, as shown in FIG. 16. The inclusion of the position adjustment mechanism 41 in the structure makes it possible to execute a fine adjustment by reflecting apparatus conditions such as the condition of the apparatus adjustment. As in the case of the illuminating optical system 13, a fine adjustment in the phase difference change in the range of 1/(several 10 s) of the illuminating wavelength λ in reality. Furthermore, in much the same way as in the illuminating optical system 13, adjustment can be executed in correspondence to any change in the distribution of the rotation of the polarization plane induced when, for instance, the wavelength of the illuminating light is altered.

As explained above, in the light-receiving optical system 14, too, the presence of the polarization correcting plate 10 disposed therein makes it possible to correct the inclination of the extent of rotation of the polarization plane along a section of the light flux induced at the concave reflecting mirror 36 and thus, the regular reflected light L2 from the wafer can be guided to the image-capturing element 39 without altering the distribution of the polarization plane in the regular reflected light. As a result, the apparatus achieving a high level of detection accuracy can be provided.

In the embodiment, the concave reflecting mirror 36 having the aluminum reflecting surface is the sole optical member disposed between the wafer 20 and the polarization plate 38. Only a very small extent of rotation of the polarization plane, e.g., a few degrees, is induced at the concave reflecting mirror 36 (a 3° rotation of the polarization plane is equivalent to a phase change of 1/60 of the wavelength λ of the illuminating light).

As explained above, since the parallel light flux is converted to a convergent light flux by using the concave reflecting mirror 36 as an off axis reflecting mirror, the light flux enters at various points of the concave reflecting mirror 36 with varying angles of incidence relative to the normal line (the values of the angles of incidence indicate an inclination on the left side and the right side of the concave reflecting mirror 36 in FIG. 15) and thus an inclination manifests with regard to the rotation of the polarization plane in the embodiment. The angle of the rotation of the polarization plane is very small. In order to achieve uniformity in the distribution of the rotational angles, the polarization correcting plate 10, too, needs to manifest a similar phase difference with a very small inclination. As has been explained in reference to the first embodiment, when a light flux enters a glass surface at an angle, the phase difference attributable to the p-polarized light and the phase difference attributable to the s-polarized light do not match. The second embodiment, too, takes advantage of this discrepancy in the phase differences so as to create the required inclination of the phase difference by disposing the plane parallel glass plate at a tilt relative to the nonparallel light flux. In addition, since the angle of inclination and the direction of inclination of the plane parallel plate are adjustable and the extent of the inclination of the phase difference can be adjusted in the order of 1/(several 10 s) to 1/100 of the wavelength λ, a fine adjustment reflecting conditions of the particular illuminating device in use is enabled. The embodiment achieves an additional advantage in that it remains free of any adverse effect of the machining error (normally manifesting to an extent of approximately 10%) which should be expected to occur at a regular phase plate.

Third Embodiment

The surface inspection apparatus achieved in the third embodiment, which includes the illuminating optical system explained in reference to the first embodiment and the light-receiving optical system explained in reference to the second embodiment is now explained in reference to FIG. 15.

The illuminating optical system 13 adopts a structure similar to that having been explained in reference to the first embodiment. The polarization plate 34 is disposed in the vicinity of the emission area of the light guide fiber 33 to convert the illuminating light L1 emitted from the light guide fiber 33 to linearly polarized light. The light having been converted to linearly polarized light at the polarization plate 34 travels through the polarization correcting plate 9 to be detailed later, and is collimated at the concave reflecting mirror 35. The wafer 20 is illuminated with the collimated linearly polarized light. Since it is highly advantageous to acquire an image of the entire wafer surface in a batch for purposes of improved throughput, the light flux from the light source is expanded and then is collimated at the concave reflecting mirror 35, as described above, so as to illuminate the entire wafer surface in the embodiment. The collimated linearly polarized light L1 having entered the wafer 20 is reflected at the surface of the wafer and then enters the light-receiving optical system 14. The structure of the light-receiving optical system 14 is similar to that having been explained in reference to the second embodiment. The light flux L2 reflected off the wafer 20 enters the concave reflecting mirror 36 and is subjected to the convergence effect, the convergent light flux travels through the polarization correcting plate 10 to be detailed later and the polarization plate 38 disposed at a position achieving a crossed Nicols relationship with the polarization plate 34, and the convergent light flux finally forms an image of the surface of the wafer 20 through the image forming lens 37 onto the image-capturing surface of the image-capturing element 39 disposed at a position conjugate with the position of the surface of the wafer 20.

At the surface of the wafer 20, a plurality of chip areas 21 are arrayed along the X direction and the Y direction, as shown in FIG. 2, with a repetitive pattern 22 formed inside each chip area 21. The repetitive pattern 22 is a resist pattern (e.g., a wiring pattern) having a plurality of line portions 2A and a plurality of space portions 2B arrayed with a constant pitch P along the direction in which their shorter sides extend (along the X direction) as shown in FIG. 3.

The stage 11 holds fast the wafer 20 having the pattern described above and placed at the surface thereof through vacuum suction or the like. The stage 11 is allowed to rotate around a specific rotational axis extending orthogonally to the stage surface by a stage rotating mechanism 16. The stage rotating mechanism 16 makes it possible to set the angle formed by the direction along which the longer side of the repetitive patterns formed at the surface of the wafer 20 extends relative to the plane of vibration of the linearly polarized light of the light flux L1 illuminating the wafer 20 to a desired angle.

In addition, the surface inspection apparatus in FIG. 15 includes the alignment system 12 disposed between the concave reflecting mirror 35 and the concave reflecting mirror 36 to detect the azimuth of the patterns formed at the surface of the wafer 20 placed on the stage 11. The alignment system 12 detects the angle formed by the plane of vibration of the linearly polarized light of the light flux L1, which is set in advance, and the direction Y along which the longer side of the repetitive pattern 22 extends, and thus, the azimuth of the direction Y along which the longer side of the repetitive pattern extends relative to the illuminating optical system 13 and the light-receiving optical system 14 can be adjusted via the stage rotating mechanism 16. The principle of the defect inspection executed in the embodiment is similar to the principle explained earlier in relation to the surface inspection apparatus. By constituting the surface inspection apparatus 30 with the illuminating optical system having been explained in reference to the first embodiment and the light-receiving optical system having been explained in reference to the second embodiment with the polarization correcting plates 9 and 10 disposed to correct the rotation of polarization plane induced at the two concave reflecting mirrors 35 and 36, a phase change is achieved as needed, as explained earlier, to match the angles of the rotations of the polarization planes. As a result, a surface inspection apparatus that minimizes the extinction ratio of the two polarization plates 34 and 38 disposed by adopting a crossed Nicols configuration can be provided.

In the surface inspection apparatus shown in FIG. 15, the image of the wafer 20 obtained via the illuminating optical system and the light-receiving optical system disposed so as to minimize the extinction ratio is captured at the image-capturing element 39 disposed at a position conjugate with the position of the surface of the wafer 20 and the captured image is then converted to a digital image. The image thus obtained indicates varying brightness values corresponding to different pattern areas, depending upon the overall form, the actual pitch and the form of a side surface of the repetitive pattern formed at the wafer surface. The digital image is then provided to the image processing device 15, which executes image processing on the image having been taken in at the image-capturing element 39 and detects brightness values in correspondence to the individual pattern areas. Since the extent to which the polarization plane rotates becomes inconsistent at an area where an error such as defocusing of the exposure device, an error in the exposure quantity or the like manifests compared to an area over which the exposure is executed in a desirable manner, a difference manifests with regard to the brightness in the resulting image. The image processing device 15 detects such differences based upon the extracted brightness values, and the defect inspection is thus executed.

In addition, if it is necessary to illuminate the wafer with a linearly polarized light flux achieving complete uniformity in the azimuth angle of the polarized light by using the illuminating optical system 13, a specific phase plate, for instance, may be disposed on the rear side of the polarization plate so as to achieve a phase difference that will cause rotation at the polarization correcting plate 9 to the opposite side from the rotation of the polarization plane induced by the concave reflecting mirror 35.

As described above, by using the surface inspection apparatus achieved in the embodiment, the rotation of the polarization plane within the planes of the concave reflecting mirror disposed in the illuminating system which illuminates the wafer and the concave reflecting mirror disposed in the light-receiving system which receives light from the wafer is adjusted with the polarization correcting plate 9 and the polarization correcting plate 10 respectively. Thus, since the inconsistency in the extinction ratio attributable to the illuminating optical system and the light-receiving optical system is eliminated, the extinction ratio improves over the entire plane of a section of the light flux, which, in turn, reduces noise to enable a highly accurate detection of even a slight change in the polarization state caused by the form birefringence.

It is desirable that position adjusters 40 and 41 capable of setting a desirable angle of inclination and a desirable direction of inclination be disposed at the polarization correcting plate 9 and the polarization correcting plate 10 respectively, as shown in FIG. 16. The inclusion of the position adjuster in the structure makes it possible to adjust even a slight extent of inconsistency attributable to the apparatus. In addition, by adjusting either of or both of the angle of inclination and the direction of inclination in correspondence to the extent of the change occurring in the extent of rotation of the polarization plane or the change in the distribution induced at the concave reflecting mirror 35 when polarization plates 34 and 38 are rotated or when the illuminating light wavelength is altered at the light source 31 and the wavelength selection filter, the extent to of the phase correction can be adjusted. Furthermore, a fine adjustment can be executed by reflecting apparatus conditions such as, for instance, the condition of the apparatus adjustment. The position adjustment mechanisms actually achieve adjustments including a fine adjustment in the phase difference change range of 1/(several 10 s) of the illuminating wavelength $\lambda$.

Fourth Embodiment

The surface of an optical system with magnifying or reducing power such as a concave reflecting mirror or a lens has a curvature, and for this reason, the angle of incidence (or the angle of emergence) of divergent light (or convergent light) at an optical surface does not change linearly along a section of the light flux, strictly speaking. Thus, the extent to which the polarization plane of the light flux having passed through the optical system rotates does not actually change linearly along the section of the light flux.

While the polarization can be corrected to a sufficient degree simply by disposing the plane parallel polarization correcting plates 9 and 10 at a tilt if the curvatures of the optical systems are relatively gentle, as in the first through third embodiments described above, it is more desirable to adopt the structure to be explained in reference to the fourth embodiment in relation to the polarization correcting plates 9 and 10 in the first through third embodiments if the curvatures of the optical systems are acute or if more accurate correction needs to be achieved.

Figure 17:
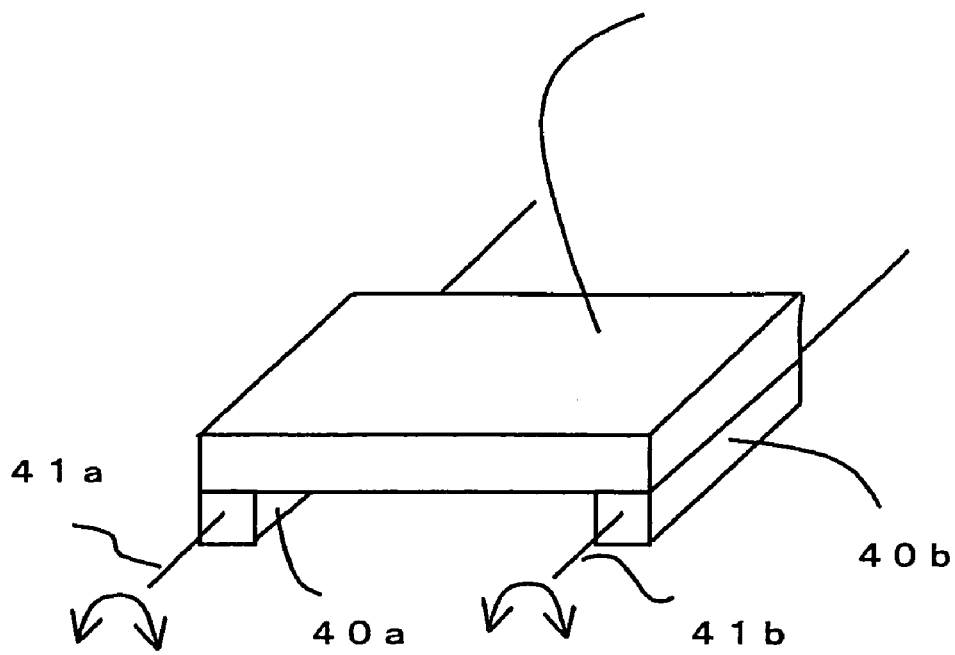
FIG. 17 shows the polarization correcting plate 9' and 10' used in a fourth embodiment.

FIG. 17 shows a polarization correcting plate 9' or 10' achieved in the embodiment. The polarization correcting plates 9' and 10' may each be constituted with a plane parallel glass plate with the two ends thereof secured with support members 40a and 40b. The support members 40a and 40b are allowed to rotate around axes 41a and 41b respectively, and by rotating either one of or both of the support members 40a and 40b, stress can be applied to the polarization correcting plate 9' or 10'. As stress is applied to the polarization correcting plate 9' or 10', it becomes deformed. In other words, stress-strain is set at the polarization correcting plate 9' or 10'. For instance, the polarization correcting plate 9' is disposed so that its plane of incidence (and its plane of emergence) ranges perpendicular to the optical axis AX1 (AX2) of the illuminating light L1 when no stress is applied thereto. (Or it is disposed at a tilt in correspondence to the surface contour of an optical system with a large radius of curvature. In such a case, a holding member 40 (41) such as that shown in FIG. 16 may be further incorporated.) However, as stress is applied and the surface contour becomes deformed, at least part of the plane of incidence (the plane of emergence) becomes tilted relative to the optical axis AX1 (AX2). (If the polarization correcting plate is disposed at a tilt, the extent of the inclination of at least part of the initial plane becomes altered.)

The light flux L1 having been emitted from the light guide fiber 11 and having been converted to linearly polarized light via the polarization plate 34 then enters the polarization correcting plate 9'. The light flux L1 is a divergent light flux at this point, and a plane of incidence at a tilt relative to the optical axis AX1 is present at the polarization correcting plate 9'. Thus, the angle of incidence of the light flux entering the polarization correcting plate 9' manifests an inclination over a section of the light flux. For this reason, the phase difference between the p component and the s component in the illuminating light L1 having been transmitted through the polarization correcting plate 9' changes in correspondence to the angle of incidence of the incident light, resulting in rotation of the polarization plane.

The plane of polarization of the illuminating light L1 illuminating the wafer 20 represents the sum of the extent of rotation at a polarization plane induced at the polarization correcting plate 9' and the extent of rotation of a polarization plane induced at the concave reflecting mirror 35. Accordingly, by deforming the polarization correcting plate 9' and thus tilting it relative to the optical axis AX1 of the illuminating optical system so as to induce a rotation of the polarization plane with an inclination toward the opposite side from the inclination of the rotation of the polarization plane induced at the concave reflecting mirror 35, the extent of rotation of the polarization plane can be a set to a uniform value. Since the same principle applies with respect to the polarization correcting plate 10' included in the light-receiving optical system 14, an even higher level of uniformity can be achieved in the extent of rotation of the polarization plane by individually deforming the two polarization correcting plates.

The support members 40a and 40b retaining the polarization correcting plates 9' and 10' can each be fixed in a specific state after it has been rotated. Accordingly, they can each be fixed at a desired rotational position (i.e., in a state having a given level of stress applied thereto)

Figure 18:
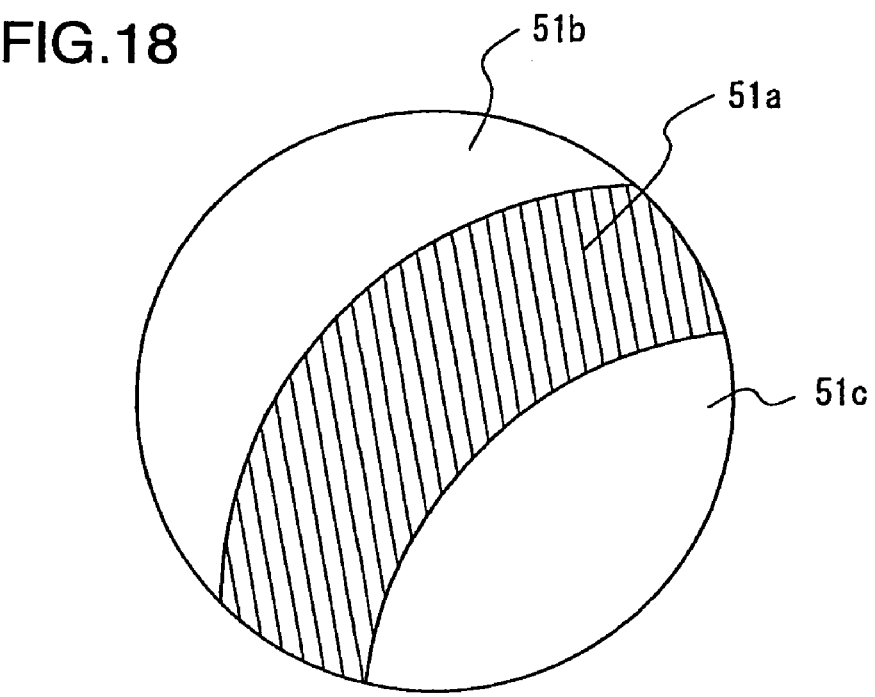
FIG. 18 shows the captured image of a bare wafer manifesting extinction irregularity.

Next, the method of adjustment executed to achieve uniformity in the values of rotation extent of the polarization plane is explained. First, a bare wafer (a wafer that has not undergone any surface treatment) is placed on the stage 11 with no stress applied to the polarization correcting plate 9' or 10'. Since no patterns are formed at the surface of the bare wafer, no elliptical polarization component is generated even if the bare wafer is irradiated with the linearly polarized light L1. Thus, theoretically, a light flux having the same polarization direction as the linearly polarized light L1 enters the polarization plate 38, which means that there is no polarization component that is transmitted through the polarization plate 38 and no light thus enters the image-capturing element 39. However, the rotation of the polarization plane occurring at the concave reflecting mirrors 35 and 36 as described earlier results in a polarization component that has manifested in an area where a polarization plane has rotated entering the image-capturing element 39 and the corresponding image portion appears bright in the image. FIG. 18 shows a captured image of the bare wafer, which includes a black strip area 51a and areas 51b and 51c that look brighter than the area 51a. The polarization planes have rotated over the areas 51b and 51c. As a result, inconsistency in the brightness (inconsistency in the extinction ratio) has occurred.

By rotating the support members 40a and 40b supporting the polarization correcting plates 9' and 10', stress is applied to the polarization correcting plates 9' and 10' to cause them to become deformed. Then, while observing the image of the bare wafer captured by the image-capturing element 39, the rotational positions of the support members 40a and 40b at which there is no longer any inconsistency in the brightness such as that shown in FIG. 18 are determined. The support members 40a and 40b are fixed at the positions at which no inconsistency in the brightness manifests.

A wafer having patterns formed thereupon is placed on the stage and inspected in this state.

While plane parallel glass plates are used as the polarization correcting plates 9' and 10' in the embodiment, members assuming another form may be used as the polarization correcting plates, as long as they are allowed to become deformed in response to stress so as to correct inconsistency in the brightness.

Variations

While the present invention is adopted in a surface inspection apparatus that detects defects by using light resulting from form birefringence in the embodiments described above, the present invention may also be adopted in a hole pattern inspection method achieved by using polarized light. In such a variation, the inspection is executed by using diffraction light as well as regular reflected light. An inspection executed by using diffraction light will require a tilt mechanism (not shown) disposed at the stage 11 in FIG. 15. This tilt mechanism adjusts the angle of the stage 11 by, for instance, tilting the stage 11 around a rotational axis AX11 perpendicular to the drawing sheet so as to enable the light-receiving optical system to take in diffraction light of a given degree generated from a repetitive pattern on the wafer 10. A regular reflected light flux, on the other hand, is mainly used when detecting defects based upon form birefringence.

In addition, while the illuminating optical system and the light-receiving optical system each include a polarization correcting plate so as to eliminate the rotational inconsistency at the polarization plane both at the illuminating optical system and the light-receiving optical system in the embodiments described above, only either the illuminating optical system or the light-receiving optical system may include a polarization correcting plate to be used to simultaneously correct the phase shifts having occurred at the concave reflecting mirror 35 and the concave reflecting mirror 36. Since the phase shifts may not always be completely corrected with a single polarization correcting plate, depending upon its off-axis direction or its off-axis angle, a polarization correcting plate is inserted in each of the two systems, i.e., the illuminating system and the light-receiving system in the embodiments to correct the phase shifts independently of each other and adjust the rotational angles of the polarization planes with a higher degree of reliability, thereby achieving an improvement in the extinction ratio. For this reason, it is more desirable to correct the phase shifts independently of each other, a single polarization correcting plate configuration or a double polarization correcting plate configuration should be selectively adopted by taking into consideration the positions at which the concave reflecting mirrors are disposed and the specifications that need to be conformed to. While the concave reflecting mirrors are each disposed as shown in FIGS. 13A and 13B in the first embodiment and the second embodiment so that the light flux is reflected at a reflecting surface defined by the plane of incidence A4 (A5) and a plane perpendicular to the plane of incidence and containing the optical axis O35 of the concave reflecting mirror over an area where the direction of its diameter overlaps with the plane of incidence, a light flux may instead be reflected over an area that does not contain either the plane of incidence or the plane perpendicular to the plane of incidence and containing the optical axis of the concave reflecting mirror. In such a case, the polarized light rotates over an angle with a greater range than the plane containing the plane of incidence, but uniformity in the distribution of the rotation of the vibration plane over a section of the light flux can be achieved through correction by disposing a polarization correcting plate at a tilt so as to cancel out the inclination of the extent of rotation of the vibration plane, as in the first embodiment and the second embodiment.

In addition, aberration (astigmatism) occurs due to the tilts with which the polarization correcting plate 9 and the polarization correcting plate 10 each constituted with a plane parallel glass plate are inserted in the diverging system and the converging system. It is desirable to reduce the extent of aberration by reducing the angle of inclination or reducing the thickness of each glass plate. The angle of inclination may be reduced by raising the refractive index of the plane parallel plate. While the refractive index of common optical glass with a low refractive index, e.g., BK7, is 1.5, there are flint-type glass products with higher refractive indices of up to nearly 2.0, and one of such products may be used to reduce the extent of aberration. Alternatively, a thin film constituted of a material with a high refractive index may be deposited (coated) over the surface of glass with a low refractive index. The overall phase shift manifesting in this case represents the sum of the phase shift attributable to the difference between the refractive indices of the deposited material and air at their interface and the phase shift attributable to the difference between the refractive indices of the deposited material and the glass at their interface. The difference between the refractive indices of the deposited material and the glass is smaller than the difference between the refractive indices of the deposited material and air, and thus, the overall phase shift predominantly reflects the phase shift occurring at the interface of the deposited material and air. Accordingly, an effect comparable to that achieved by using a plane parallel plate constituted of glass with a high refractive index is realized. A reflection increasing film may be formed by combining glass and a deposit material with specific thicknesses to result in a lowered transmittance. If this is not desirable, a material with a high refractive index should be deposited on glass with a high refractive index. The effect achieved by combining glass and a deposit material with refractive indices equal to each other is equivalent to the effect achieved with the use of the glass alone. By depositing a thin film, an added advantage is achieved in that tarnishing which tends to occur on glass with a high refractive index, is prevented.

In addition, the polarization correcting plates 9 and 10 may be constituted with transparent plastic instead of glass. The material to constitute the plane parallel plates should be selected so as to satisfy the requirements stipulated in the specifications.

Figure 19:
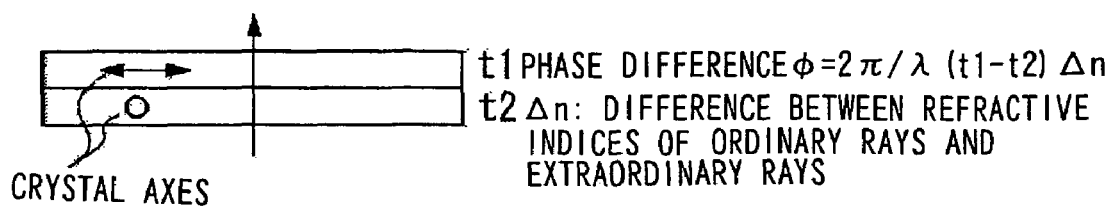
FIG. 19 illustrates a polarization correcting plate.

Furthermore, the polarization correcting plates 9 and 10 may each be formed by pasting together two birefringent crystal plane parallel plates such as quartz plates as shown in FIG. 19, with the two plates set so that the crystal axes extend perpendicular to each other, instead of by using a glass plane parallel plate. In this case, the rotation of the polarization plane induced at the concave reflecting mirror can be canceled out with the phase difference attributable to the thicknesses of the crystals and the difference between the refractive indices of the ordinary rays and the extraordinary rays. With t1 and t2 representing the thicknesses of the two crystals and $\Delta n$ representing the difference between the refractive indices of the ordinary rays and the extraordinary rays at the crystals, the phase difference $\phi$ is calculated as;

$$\phi = 2\pi/\lambda \cdot (t1-t2)\Delta n$$

Figure 20:
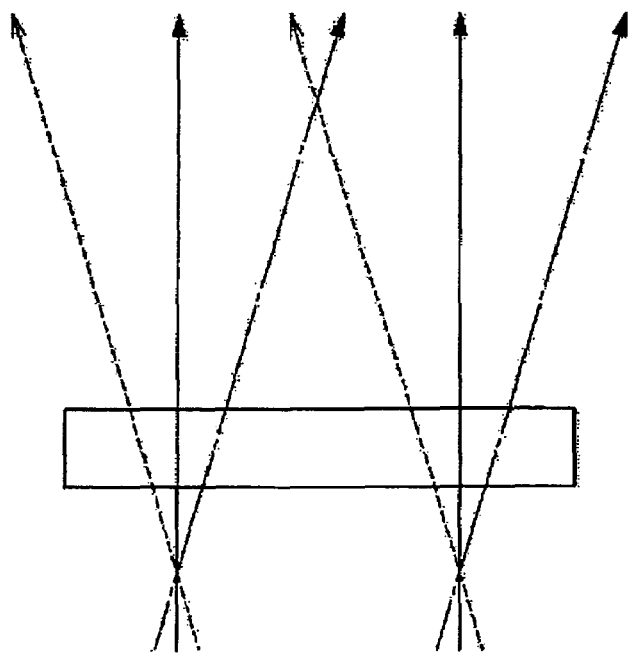
FIG. 20 is a schematic illustration of light fluxes passing through the polarization correcting plate.
Figure 21:
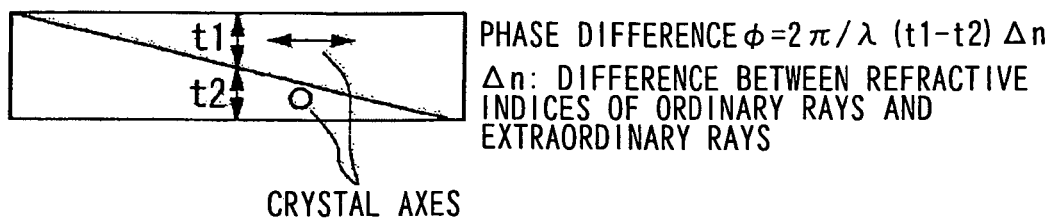
FIG. 21 illustrates a polarization correcting plate.
Figure 22:
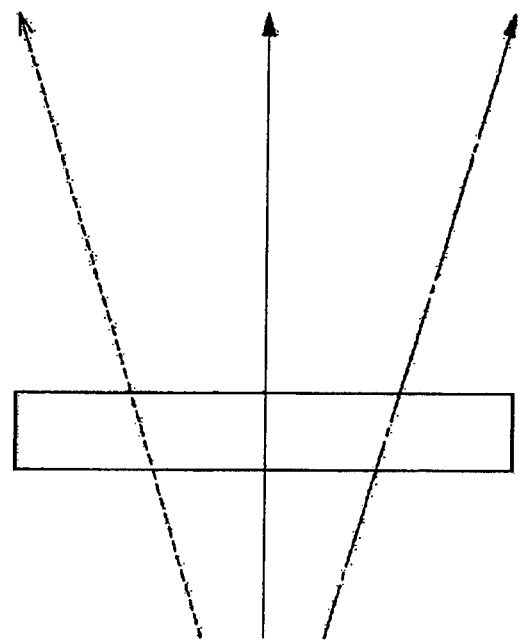
FIG. 22 is a schematic illustration of light fluxes passing through the polarization correcting plate.

Since the polarization correcting plates 9 and 10 are each disposed in a pupil space, the angle formed by the polarization correcting plate relative to the optical axis of the light flux is equivalent to a position on the wafer. The diameter of the light flux in the pupil space is equivalent to the numerical aperture (NA) on the wafer. While it is desirable to constitute a polarization correcting plate with a plane parallel glass plate or by pasting crystal plate as described above when the light flux diameter is significant, as shown in FIG. 20, it maybe constituted by using a Babinet's compensator if the light flux diameter is small, as shown in FIG. 22. A Babinet's compensator is a plane parallel plate achieved by pasting together two wedge prisms constituted of birefringent crystal, such as quartz, as shown in FIG. 21, with the crystal axes of the two prisms set perpendicular to each other. While the Babinet's compensator induces a phase difference as indicated in the expression presented earlier, the value of $t1-t2$ changes at the position at which the light flux passes through the compensator depending upon the angle of the wedges. For this reason, varying phase differences can be achieved each in correspondence to a specific angle to cancel out the rotations of the polarization planes induced at the concave reflecting mirror, in much the same way as that explained earlier.

However, if the light flux diameter is large, as shown in FIG. 20, different phase differences manifest in conjunction with light rays achieving angles equal to one another (light rays that illuminate a single position on the wafer, are reflected at a single position on the wafer or are diffracted at a single position on the wafer, indicated with the solid line, the dotted line and the one-point chain line), depending upon the positions at which they pass through the phase plate, and for this reason, the extinction ratio cannot be uniformly improved.

Accordingly, the optimal type of correcting plate should be selected by taking into consideration the diameter of the light flux diameter. While the use of birefringent crystal is not ideal if the angle of incidence is large, birefringent crystal may be used quite effectively if the angle of divergence and the like at the apparatus are relatively small. The optimal material should be selected so as to meet particular needs in the apparatus.

While an explanation has been given in reference to all the embodiments of the present invention on an example in which a concave reflecting mirror is utilized both in the illuminating optical system and the light-receiving optical system, an inclination in the extent of rotation of the polarization plane taken along a section of the light flux is induced when divergent light or convergent light enters a reflecting mirror, a refracting optical system or a reflecting/refracting optical system disposed at a tilt instead of a concave reflecting mirror. Obviously, the structure according to the present invention may be adopted in conjunction with any of these optical systems to achieve uniformity in the extent of rotation of the polarization plane taken along a section of the light flux.

The above described embodiments are examples, and various modifications can be made without departing from the spirit and scope of the invention.

What is claimed is:

1. A surface inspection apparatus comprising:
   a light source unit that emits a divergent light flux of predetermined linearly polarized light to be used to illuminate a test substrate;
   an optical member that allows the divergent light flux of the predetermined linearly polarized light to enter therein with a principle ray of the divergent light flux achieving a predetermined angle of incidence and then guides a light flux to the test substrate;
   a light-receiving unit that receives linearly polarized light in a light flux from the test substrate, which is polarized along a direction perpendicular to a polarization direction of the predetermined linearly polarized light;
   at least one polarization correcting member disposed within a light path extending between the light source unit and the light-receiving unit, which corrects a disruption of a polarization plane attributable to the optical member; and
   an inspection unit that inspects a surface of the test substrate based upon the light received at the light-receiving unit.

2. A surface inspection apparatus comprising:
   a light source unit that emits a light flux of predetermined linearly polarized light to be used to illuminate a test substrate;
   an optical member disposed at a position that allows a light flux from the test substrate to enter the optical member, through which the light flux from the test substrate is emitted as a convergent light flux with a principle ray of the convergent light flux achieving a predetermined angle of emergence;
   a light-receiving unit that receives linearly polarized light in the convergent light flux from the optical member, which is polarized along a direction perpendicular to a polarization direction of the predetermined linearly polarized light;
   at least one polarization correcting member disposed within a light path extending between the light source unit and the light-receiving unit, which corrects a disruption of a polarization plane attributable to the optical member; and
   an inspection unit that inspects a surface of the test substrate based upon the light received at the light-receiving unit.

3. A surface inspection apparatus comprising:
   a light source unit that emits a divergent light flux of predetermined linearly polarized light to be used to illuminate a test substrate;
   a first optical member that allows the divergent light flux of the predetermined linearly polarized light to enter therein with a predetermined angle of incidence and then guides a light flux to the test substrate;
   a second optical member that allows a light flux from the test substrate to enter therein, emits a convergent light flux thereof with a predetermined angle of emergence and forms an image at a specific surface;
   an extraction unit that extracts linearly polarized light in the convergent light flux from the second optical member, which is perpendicular to the predetermined linearly polarized light;
   a light-receiving unit that receives an image of the test substrate formed via the second optical member and the extraction unit; and
   at least one polarization correcting member disposed within a light path extending between the light source unit and the light-receiving unit, which corrects a disruption of a polarization plane attributable to the first optical member and the second optical member.

4. A surface inspection apparatus according to claim 1, wherein:
   the polarization correcting member is disposed within the divergent light flux with a tilt toward a side opposite from a direction along which the optical member is tilted relative to the principle ray of the divergent light flux.

5. A surface inspection apparatus according to claim 2, wherein:
   the polarization correcting member is disposed within the convergent light flux with a tilt toward a side opposite from a direction along which the optical member is tilted relative to the principle ray of the convergent light flux.

6. A surface inspection apparatus according to claim 1, further comprising:
   a holding member that holds the polarization correcting member so as to allow at least either a direction or an angle of tilt with which the polarization correcting member is set to be adjustable.

7. A surface inspection apparatus according to claim 2, further comprising:
   a holding member that holds so as to allow at least either a direction or an angle of tilt with which the polarization correcting member is set to be adjustable.

8. A surface inspection apparatus according to claim 1, wherein:
   the polarization correcting member is a plane parallel glass plate disposed at an inclination relative to a surface of the optical member.

9. A surface inspection apparatus according to claim 2, wherein:
   the polarization correcting member is a plane parallel glass plate disposed at an inclination relative to a surface of the optical member.

10. A surface inspection apparatus according to claim 1, wherein;
    the polarization correcting member is disposed at an inclination relative to a plane perpendicular to an optical axis of the optical member and is constituted with two birefringent plane parallel crystal plates pasted together so as to set crystal axes thereof perpendicular to each other.

11. A surface inspection apparatus according to claim 2, wherein;
    the polarization correcting member is disposed at an inclination relative to a plane perpendicular to an optical axis of the optical member and is constituted with two wedge-shaped birefringent crystals pasted together so as to set crystal axes thereof perpendicular to each other and also to form a plane parallel plate.

12. A surface inspection apparatus according to claim 1, wherein;
    the polarization correcting member is disposed at an inclination relative to a plane perpendicular to an optical axis of the optical member and is constituted with two wedge-shaped birefringent crystals pasted together so as to set crystal axes thereof perpendicular to each other and also to form a plane parallel plate.

13. A surface inspection apparatus according to claim 2, wherein;
the polarization correcting member is disposed at an inclination relative to a plane perpendicular to an optical axis of the optical member and is constituted with two wedge-shaped birefringent crystals pasted together so as to set crystal axes thereof perpendicular to each other and also to form a plane parallel plate.

14. A surface inspection apparatus according to claim 1, wherein;
stress-strain is set at the polarization correcting member disposed between the light source unit and the light-receiving unit.

15. A surface inspection apparatus according to claim 2, wherein;
stress-strain is set at the polarization correcting member disposed between the light source unit and the light-receiving unit.

16. A surface inspection apparatus according to claim 14, wherein:
the stress-strain set at the polarization correcting member can be fixed to an arbitrary value.

17. A surface inspection apparatus according to claim 15, wherein:
the stress-strain set at the polarization correcting member can be fixed to an arbitrary value.

18. A surface inspection apparatus according to claim 1, wherein:
a parallel light flux entering the optical member becomes convergent by the optical member.

19. A polarization illuminating device, comprising:
a light source unit that emits a divergent light flux of linearly polarized light;
an optical member that allows the divergent light flux of the linearly polarized light generated at the light source unit to enter therein with a predetermined angle of incidence and then guides a light flux to a test substrate; and
a polarization correcting member disposed within a light path extending between the light source unit and the test substrate, which corrects a disruption of a polarization plane attributable to the optical member.

20. A light-receiving device comprising:
an optical member that allows a light flux originating from a test substrate and containing a specific polarization component to enter therein and emits a convergent light flux thereof with a predetermined angle of emergence;
a light-receiving unit that receives linearly polarized light in the light flux from the optical member; and
a polarization correcting member disposed within a light path extending between the test substrate and the light-receiving unit, which corrects a disruption of a polarization plane attributable to the optical member.

* * * * *